(12) United States Patent
Brown et al.

(10) Patent No.: US 11,571,294 B2
(45) Date of Patent: Feb. 7, 2023

(54) INTRAOCULAR LENS INJECTOR

(71) Applicant: ALCON INC., Fribourg (CH)

(72) Inventors: Kyle Brown, Fort Worth, TX (US); Tu Cam Tran, Grapevine, TX (US); Yinghui Wu, Cedar Hill, TX (US); Stephen J Van Noy, Southlake, TX (US)

(73) Assignee: Alcon Inc., Fribourg (CH)

( * ) Notice: Subject to any disclaimer, the term of this patent is extended or adjusted under 35 U.S.C. 154(b) by 476 days.

(21) Appl. No.: 16/750,140

(22) Filed: Jan. 23, 2020

(65) Prior Publication Data

US 2020/0163754 A1 May 28, 2020

Related U.S. Application Data

(63) Continuation of application No. 15/838,946, filed on Dec. 12, 2017, now Pat. No. 10,568,735.

(60) Provisional application No. 62/469,682, filed on Mar. 10, 2017, provisional application No. 62/446,194, filed on Jan. 13, 2017.

(51) Int. Cl.
*A61F 2/16* (2006.01)

(52) U.S. Cl.
CPC ............ *A61F 2/167* (2013.01); *A61F 2/1678* (2013.01); *A61F 2/1691* (2013.01); *A61F 2/1662* (2013.01); *A61F 2/1664* (2013.01)

(58) Field of Classification Search
CPC .... A61F 2002/1681; A61F 2002/16903; A61F 2/167; A61F 2/1691; A61F 2/1678; A61F 2/1662; A61F 2/1664
See application file for complete search history.

(56) References Cited

U.S. PATENT DOCUMENTS

| | | | |
|---|---|---|---|
| 8,968,328 B2 | 3/2015 | Ichinohe | |
| 9,655,718 B2 | 5/2017 | Kudo et al. | |
| 9,877,826 B2 | 1/2018 | Kudo et al. | |
| 9,901,442 B2 | 2/2018 | Kudo et al. | |
| 9,907,647 B2 | 3/2018 | Inoue | |
| 9,980,811 B2 | 5/2018 | Kudo et al. | |
| 10,039,668 B2 | 8/2018 | Kudo et al. | |
| 2009/0248031 A1 | 10/2009 | Ichinohe | |
| 2009/0270876 A1 | 10/2009 | Hoffmann | |
| 2014/0135782 A1 | 5/2014 | Valle | |

FOREIGN PATENT DOCUMENTS

| | | |
|---|---|---|
| CN | 101511309 A | 8/2009 |
| CN | 103491907 A | 1/2014 |
| EP | 2574308 A2 | 4/2013 |
| JP | 2012011250 A | 1/2012 |
| JP | 2016189925 A | 11/2016 |
| RU | 2494704 C2 | 10/2013 |
| RU | 2506927 C2 | 2/2014 |
| WO | 2004014259 A1 | 2/2004 |

*Primary Examiner* — Anh T Dang

(57) ABSTRACT

Apparatuses, systems, and methods for implanting an intraocular lens into an eye are described. For example, an intraocular lens injector may include a passage formed in a distal end portion of the intraocular lens injector. The passage may define an interior surface, and a ramp may be formed on the interior surface so as to cause a leading haptic of an intraocular lens (IOL) being advanced through the passage to lift above a surface of an optic of the IOL to ensure proper folding of the IOL.

18 Claims, 19 Drawing Sheets

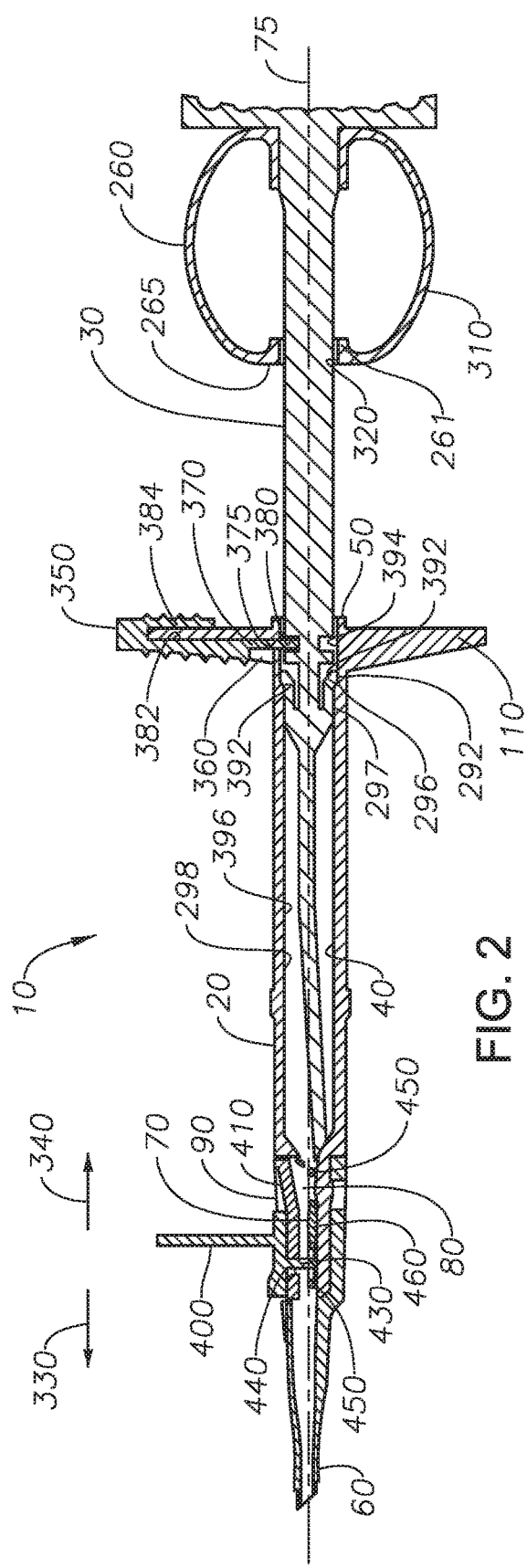
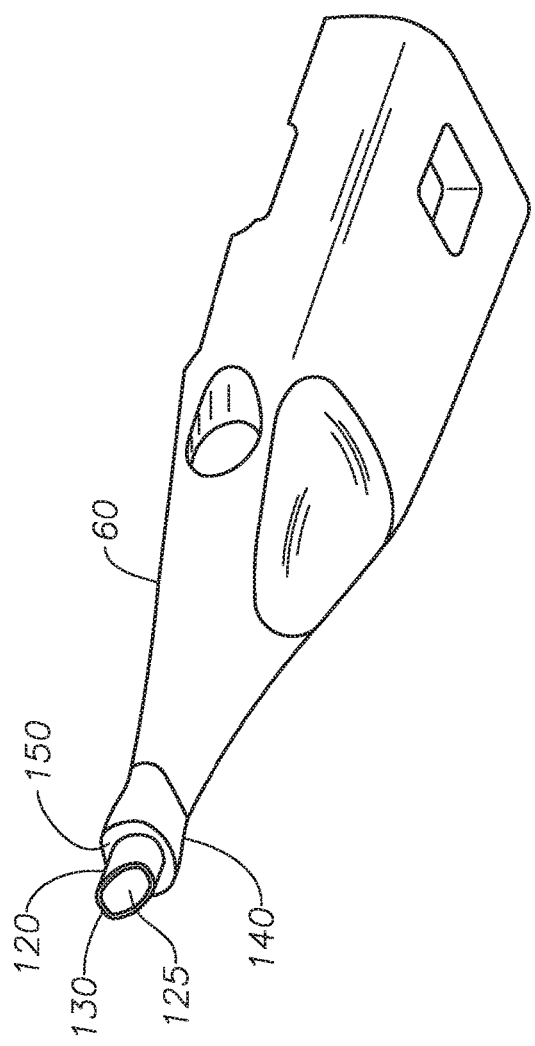
FIG. 2
FIG. 3

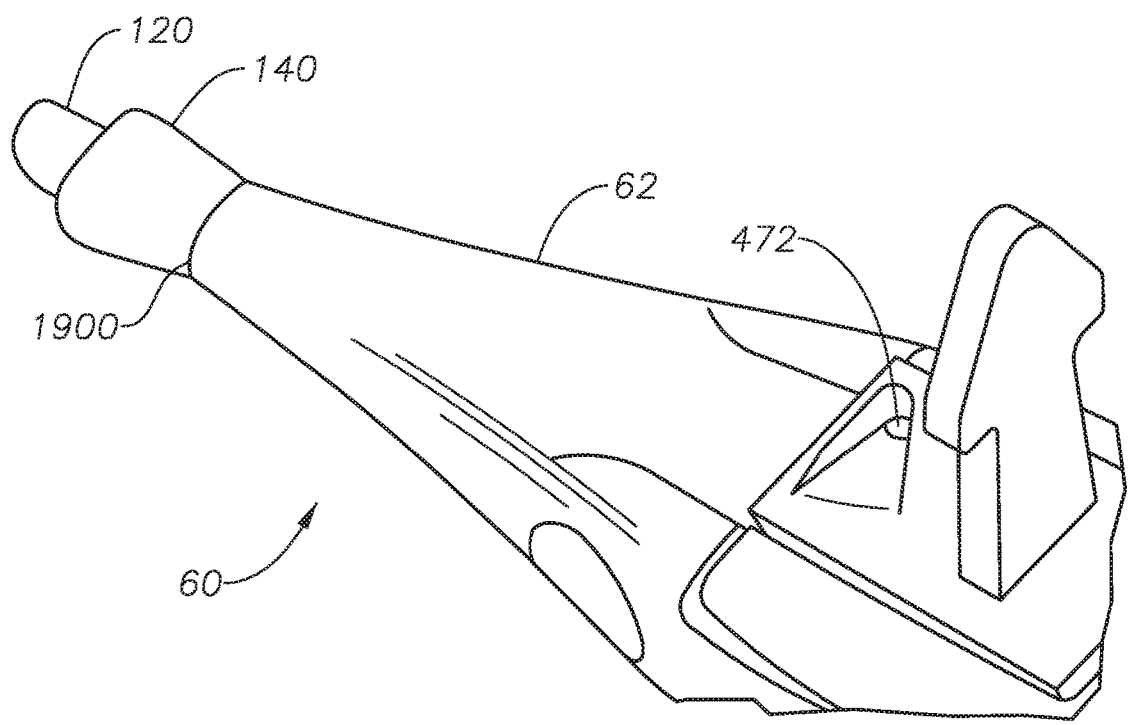
FIG. 13
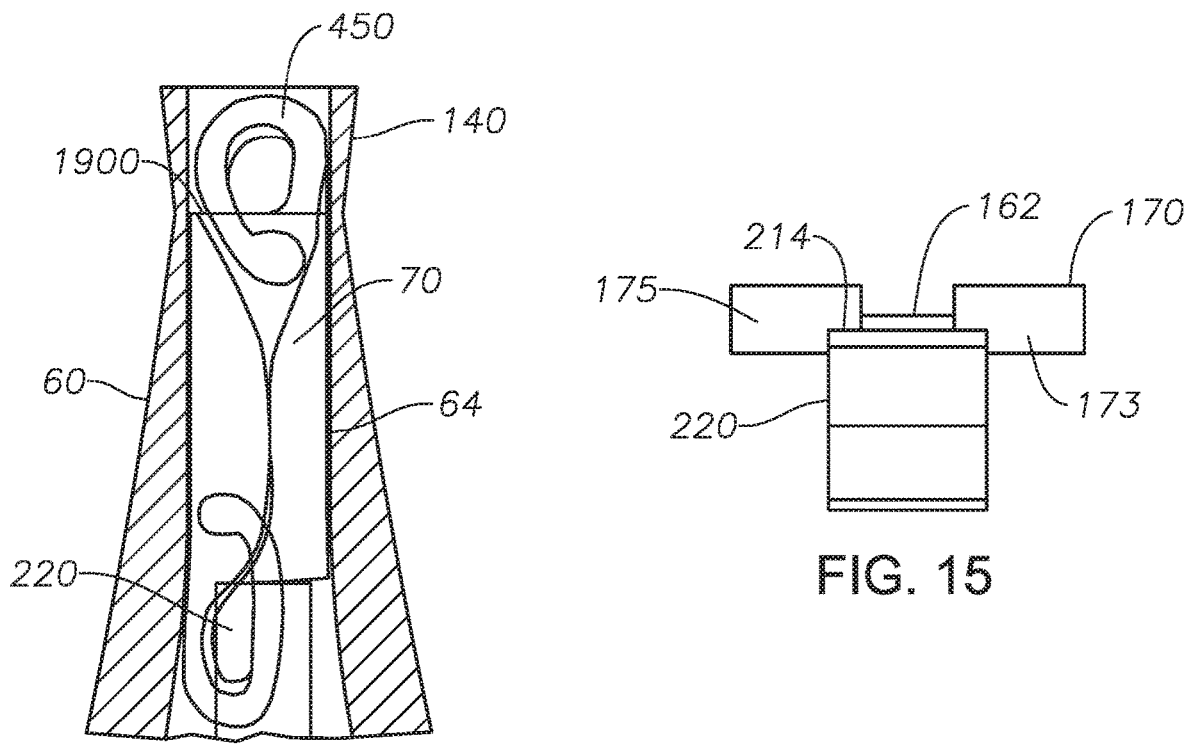
FIG. 14
FIG. 15

INTRAOCULAR LENS INJECTOR

CROSS-REFERENCE TO RELATED APPLICATIONS

This application is a continuation of U.S. application Ser. No. 15/838,946, filed Dec. 12, 2017 and claims the benefit of U.S. Provisional Application No. 62/446,194, filed Jan. 13, 2017, and claims the benefit U.S. Provisional Application No. 62/469,682, filed Mar. 10, 2017, the entire contents of each being incorporated herein by reference.

TECHNICAL FIELD

The present disclosure relates to systems, apparatuses, and methods for intraocular lens injectors. Particularly, the present disclosure relates to systems, apparatuses, and methods for intraocular lens injectors including features for lifting a leading haptic of an intraocular lens for improved intraocular lens folding performance.

BACKGROUND

The human eye in its simplest terms functions to provide vision by transmitting and refracting light through a clear outer portion called the cornea, and further focusing the image by way of the lens onto the retina at the back of the eye. The quality of the focused image depends on many factors including the size, shape and length of the eye, and the shape and transparency of the cornea and lens. When trauma, age or disease cause the lens to become less transparent, vision deteriorates because of the diminished light which can be transmitted to the retina. This deficiency in the lens of the eye is medically known as a cataract. The treatment for this condition is surgical removal of the lens and implantation of an artificial intraocular lens ("IOL").

Many cataractous lenses are removed by a surgical technique called phacoemulsification. During this procedure, an opening is made in the anterior capsule and a thin phacoemulsification cutting tip is inserted into the diseased lens and vibrated ultrasonically. The vibrating cutting tip liquefies or emulsifies the lens so that the lens may be aspirated out of the eye. The diseased lens, once removed, is replaced by an artificial lens.

The IOL is injected into the eye through the same small incision used to remove the diseased lens. An IOL injector is used to deliver an IOL into the eye.

SUMMARY

According to one aspect, the disclosure describes an intraocular lens injector that may include an injector body and a plunger. The injector body may include a bore defined by an interior wall, a longitudinal axis extending centrally along the injector body, and a distal end portion. The distal end portion may include a first sidewall; a second sidewall disposed opposite the first sidewall; a third sidewall extending between the first sidewall and the second sidewall; and a fourth sidewall opposite the third sidewall, the first sidewall, second sidewall, third sidewall, and fourth sidewall joined to define passage forming a portion of the bore. The injector body may also include a first ramp formed on an interior surface of the passage along the first sidewall and laterally offset from the longitudinal axis. The first ramp may be disposed at a position within the passage to contact a leading haptic of an intraocular lens. The first ramp may include a first leading surface being sloped and inwardly extending from the interior surface into the passage and a first peak disposed at a distal end of the first ramp disposed at a distal end of the first leading surface. The intraocular lens injector may also include a plunger slideable within the bore defined by the interior wall.

The aspects of the present disclosure may include one or more of the following features. The first leading surface may include a first plurality of steps therealong. Each of the first plurality of steps may include a rise and a run. The rise and run of each of the steps is uniform. At least one of the rise and run of at least one step of the first plurality of steps may be different from the rise and the run of another of the steps of the first plurality of steps. The injector body may also include a compartment configured to receive the intraocular lens. The compartment may adjoins and be in fluid communication with the passage. A threshold may be defined between the passage and the compartment. A proximal end of the first leading surface of first ramp may be located along at the threshold.

One or more of the following features may also be included in the various aspects of the present disclosure. A second ramp may be formed on the interior surface of the passage along the second sidewall and adjacent to the first ramp. The first ramp and the second ramp may be integrally formed. The second ramp may include a second leading surface, and the second leading surface may be sloped and extend inwardly from the interior surface of the passage. The second ramp may also include a second peak disposed at a distal end of the second leading surface. The second leading surface may include a second plurality of steps. Each of the second plurality of steps may include a rise and a run. The rise and run of each of the steps may be uniform. At least one of the rise and run of at least one step of the second plurality of steps may be different from the rise and the run of another of the steps of the second plurality of steps. The first leading surface and the second leading surface may be integrally formed. The first ramp further may include a first trailing surface disposed distally of the first peak. The first trailing surface may have a positive slope. A second ramp may be formed on the interior surface of the passage along the second sidewall and adjacent to the first ramp. The second ramp may include a second leading surface that is sloped and that extends inwardly from the interior surface of the passage, a second peak disposed at a distal end of the second leading surface, and a second trailing surface. The second trailing surface may have a positive slope. The first trailing surface and the first trailing surface may be integrally formed.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

FIG. 2 shows a longitudinal cross-sectional view of the intraocular lens injector of FIG. 1.

FIG. 3 is a perspective view of a distal portion of an example injector body of the intraocular lens injector of FIG. 1.

FIG. 13 is a detail view of the distal end portion of the IOL injector showing a demarcation designating a pause position of an IOL being advanced through the IOL injector.

FIG. 14 is a view of a distal end portion of an IOL injector with an IOL located therein at a pause position.

FIG. 15 is a detail view of an example IOL injector showing an opening at an interface between a compartment into which an IOL is received and an internal bore of an injector body, the detail view being transverse to a longitudinal axis of the IOL injector, and the detail view showing a flexible wall portion in contact with an injector rod.

DETAILED DESCRIPTION

Figure 1:
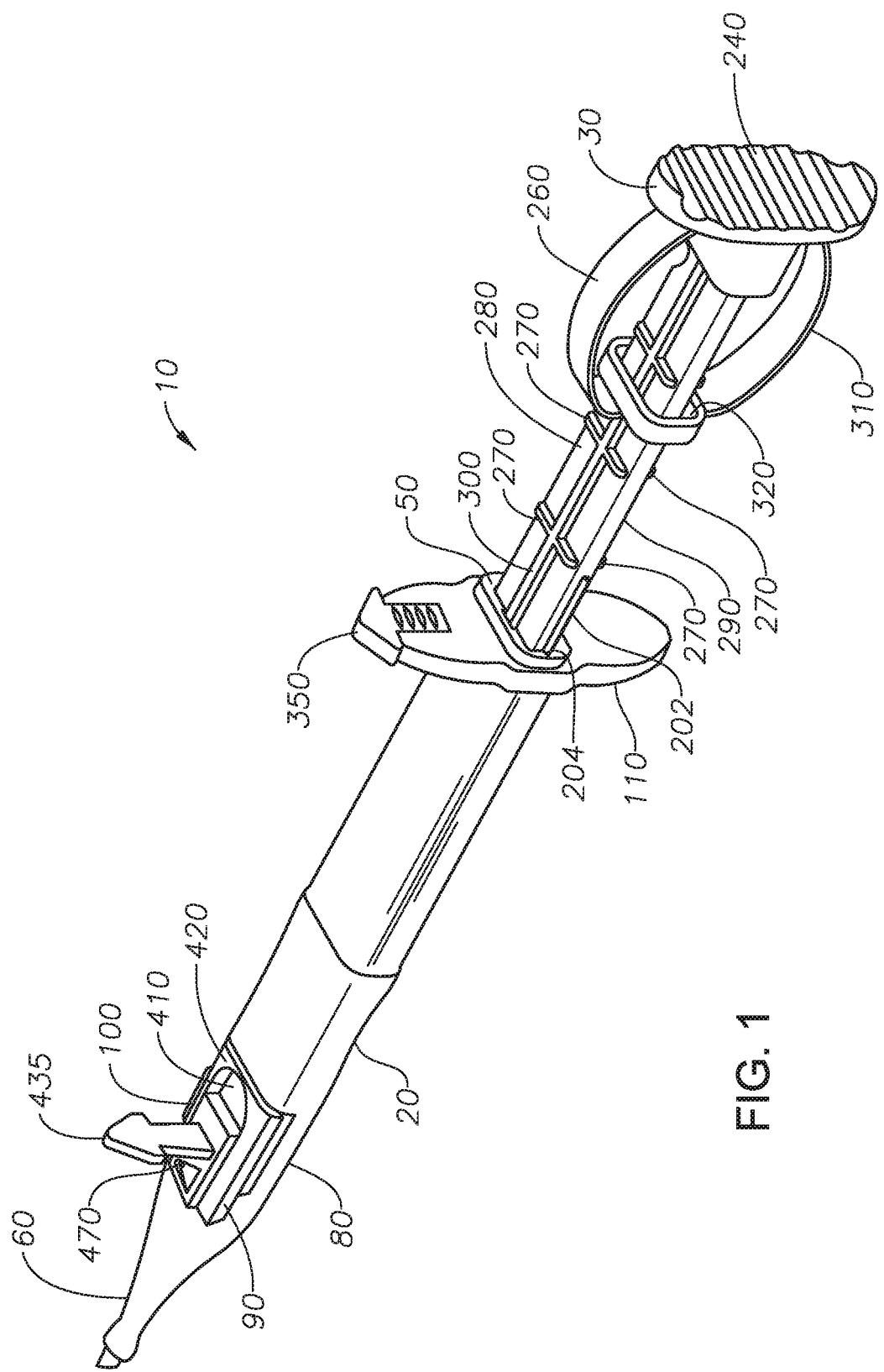
FIG. 1 is a perspective view of an example intraocular lens injector.

For the purposes of promoting an understanding of the principles of the present disclosure, reference will now be made to the implementations illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one implementation may be combined with the features, components, and/or steps described with respect to other implementations of the present disclosure.

The present disclosure relates to systems, apparatuses, and methods for delivering an IOL into an eye. Particularly, the present disclosure relates to systems, apparatuses, and methods for intraocular lens injectors having features to improve leading haptic lift during intraocular lens folding. FIGS. 1 and 2 show an example IOL injector 10 that includes an injector body 20 and a plunger 30. The injector body 20 defines a bore 40 extending from a proximal end 50 of the injector body 20 to a distal end portion 60 of the injector body 20. The plunger 30 is slideable within the bore 40. Particularly, the plunger 30 is slideable within bore 40 in order to advance an IOL, such as IOL 70, within the injector body 20. The IOL injector 10 also includes a longitudinal axis 75 disposed centrally through the body 20. The longitudinal axis 75 may extend along the plunger 30 and define a longitudinal axis of the plunger 30.

The injector body 20 includes a compartment 80 operable to house an IOL prior to insertion into an eye. In some instances, a door 90 may be included to provide access to the compartment 80. The door 90 may include a hinge 100 such that the door 90 may be pivoted about the hinge 100 to open the compartment 80. The injector body 20 may also include tabs 110 formed at the proximal end 50 of the injector body 20. The tabs 110 may be manipulated by fingers of a user, such as an ophthalmologist or other medical professional, to advance the plunger 30 through the bore 40.

Figure 4:
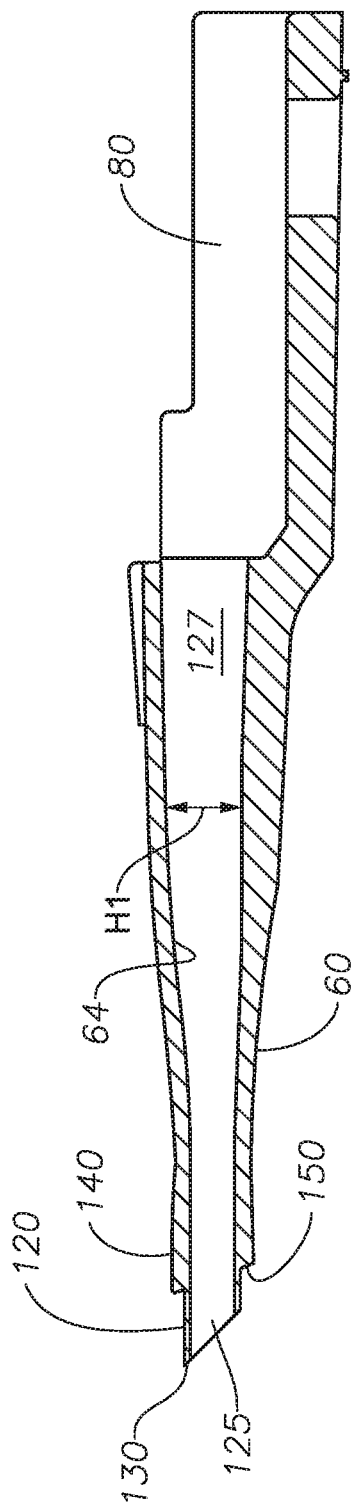
FIG. 4 is a cross-sectional view of the distal portion of the injector body shown in FIG. 3.
Figure 5:
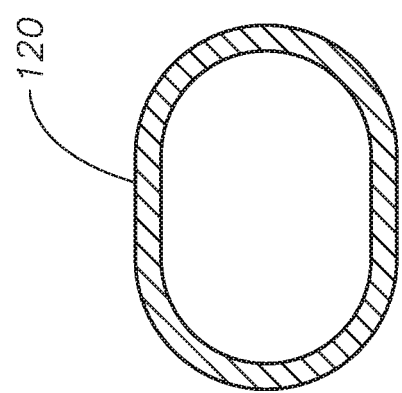
FIG. 5 is an example cross-sectional shape of a nozzle of an intraocular lens injector.

FIGS. 3-5 illustrate details of the distal end portion 60 of the injector body 20. In some instances, the distal end portion 60 has a tapered exterior surface. Further, the distal end portion 60 includes a passage 64 that tapers towards a distal opening 125. The injector body 20 also includes a nozzle 120 at the distal end portion 60. The nozzle 120 is adapted for insertion into an eye so that an IOL may be implanted. An IOL is expelled from distal opening 125 formed in the nozzle 120. As shown in FIG. 5, the nozzle 120 may have an elliptical cross section. Additionally, the nozzle 120 may include a beveled tip 130. The compartment 80, passage 64, and opening 125 may define a delivery passage 127. A size of the delivery passage 127 may vary along its length. That is, in some instances, a height H1 of the passage may change along a length of the delivery passage 127. The variation in size of the delivery passage 127 may contribute to the folding of the IOL as it is advanced therealong.

In some instances, the injector body 20 may include an insertion depth guard 140. The insertion depth guard 140 may form a flanged surface 150 that is adapted to abut an exterior eye surface. The insertion depth guard 140 abuts an eye surface and, thereby, limits an amount by which the nozzle 120 is permitted to extend into an eye. In some implementations, the flanged surface 150 may have a curvature that conforms to the outer surface of an eye. For example, the flanged surface 150 may have a curvature that conforms to a scleral surface of the eye. In other instances, the flanged surface 150 may have a curvature that corresponds to a corneal surface of the eye. In still other instances, the flanged surface 150 may have a curvature, part of which corresponds to a scleral surface and another part that corresponds to a corneal surface. Thus, the flanged surface 150 may be concave. In other instances, the flanged surface 150 may be flat. In still other instances, the flanged surface 150 may be convex. Further, the flanged surface 150 may have any desired contour. For example, the flanged surface 150 may be a curved surface having radii of curvature that vary along different radial directions from a center of the flanged surface 150. In still other instances, the flanged surface 150 may define a surface that has varying curvature along different radial directions as well as curvature that varies along one or more particular radial directions.

In FIG. 3, the insertion depth guard 140 is shown as a continuous feature that forms a continuous flanged surface 150. In some implementations, the insertion depth guard 140 may be segmented into a plurality of features or protrusions forming a plurality of eye-contacting surfaces. These eye-contacting surfaces may work in concert to control the depth to which the nozzle 120 may penetrate an eye. In other implementations, the insertion depth guard 140 may be omitted.

Figure 6:
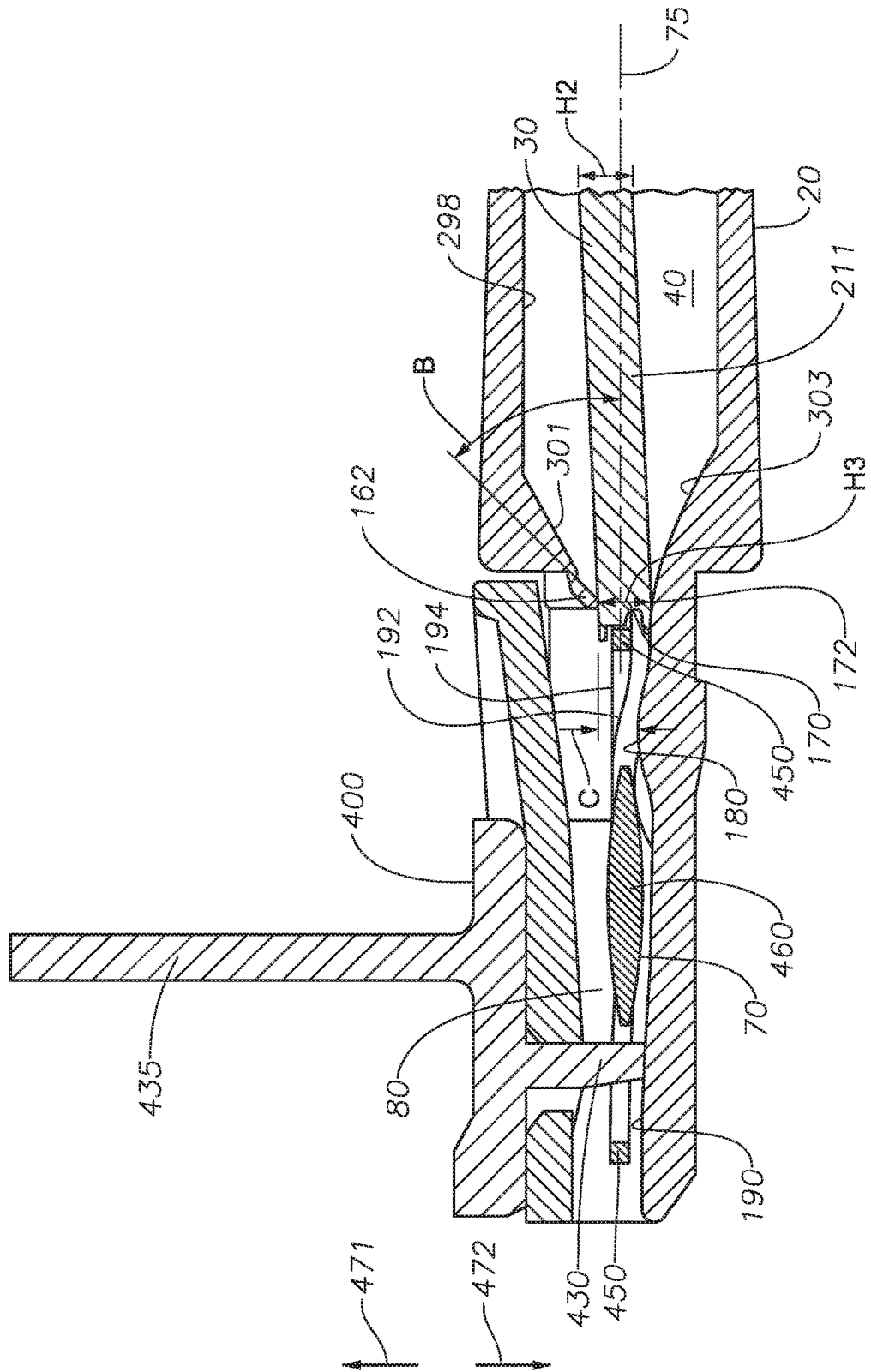
FIG. 6 shows a cross-sectional view of an intraocular lens receiving compartment formed in an injector body.
Figure 7:
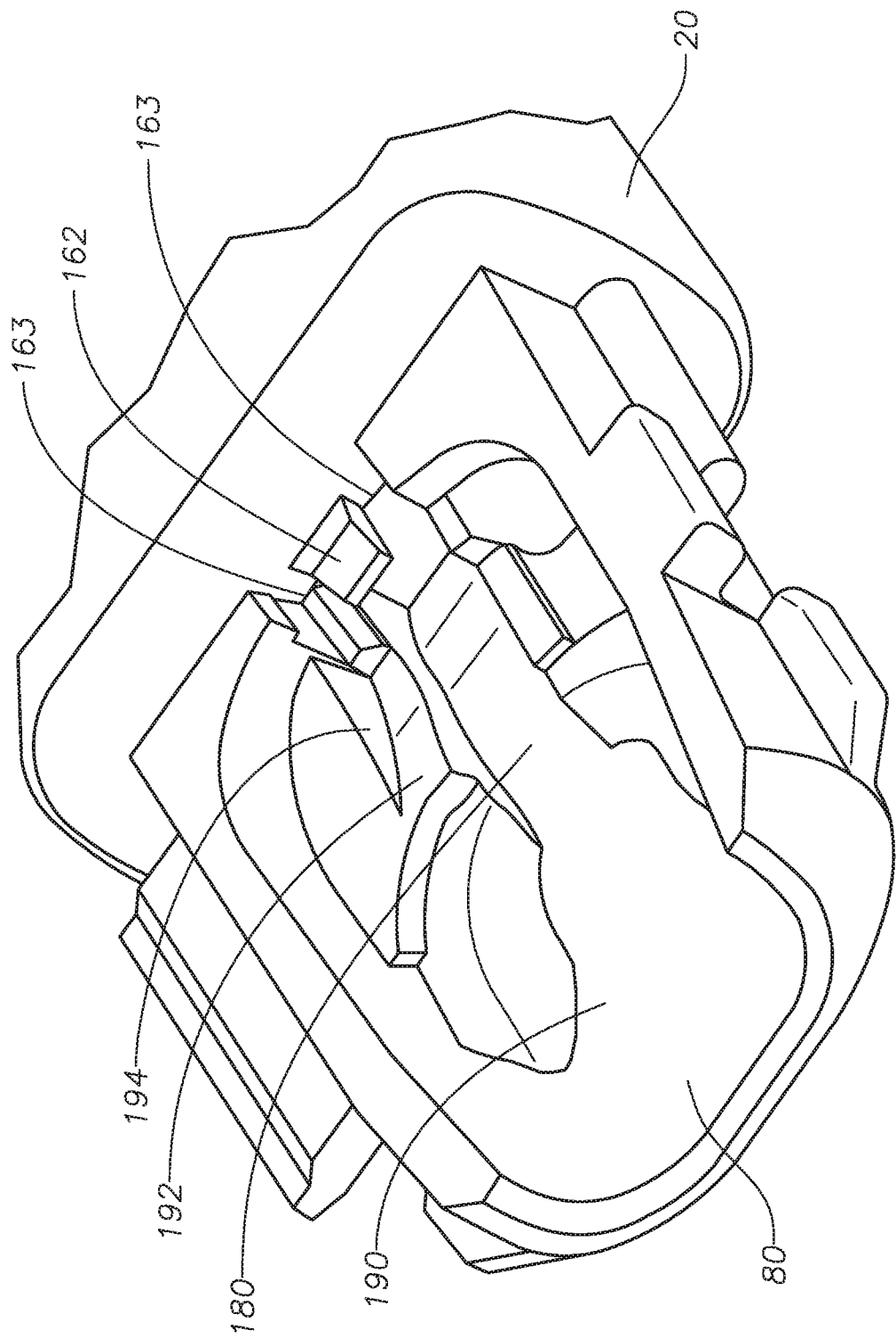
FIG. 7 shows a perspective view of an intraocular lens receiving compartment formed in an injector body.

FIG. 6 shows a cross-sectional detail view of the compartment 80 and a portion of bore 40 of the example injector body 20 shown in FIG. 2. The bore 40 is defined by an interior wall 298. The interior wall 298 includes a tapered portion that includes a first tapered wall 301 and a second tapered wall 303. The tapered portion of the interior wall 298 defines an opening 170 at an interface 172 between the bore 40 and the compartment 80. The opening 170 includes a height H2. A distal end portion 211 of the plunger rod 210 has a height of H3. In some instances, height H2 may be larger than height H3, such that, initially, there is no interference between the plunger rod 210 and the interior wall 298 at the opening 170. In other instances, height H2 may be equal to or larger than height H3, such that the plunger rod 210 and the opening 170 initially have an interference fit. In some implementations, the first tapered wall 301 includes a flexible wall portion. In the example shown, the flexible wall portion 162 is an obliquely-extending, flexible portion of the interior wall 298 and, particularly, of the first tapered wall 301. As shown in FIG. 7, in some instances, portions of the first tapered wall 301 are removed, forming voids 163 that flank the flexible wall portion 162. Thus, in some instances, the flexible wall portion 162 may extend in a cantilevered manner.

Referring again to FIG. 6, in some instances, the flexible wall portion 162 may be sloped toward the distal end portion 60 of the injector body 20. In some instances, an angle B defined by the flexible wall portion 162 and the longitudinal axis 75 may be in the range of 20° to 60°. For example, in some instances, the angle B may be 20°, 25°, 30°, 35°, 40°, 45°, 50°, 55°, or 60°. Further, the angle B may be greater or smaller than the defined range or anywhere within the recited range. Moreover, the scope of the disclosure is not so limited. Thus, the angle B may be any desired angle.

The injector body 20 may also include a contoured ramp 180 formed along an interior receiving surface 190 of the compartment 80. Generally, the interior receiving surface 190 is the surface on which an IOL, such as IOL 70, is placed when loaded into the IOL injector 10. FIG. 7 is a perspective view of a portion of the example injector body 20 shown in FIG. 2. The door 90 is not shown. In some instances, a vertical distance C between a tip of the flexible wall portion 162 and the top of the contoured ramp 180 may correspond with a height H3 of a distal end portion 211 of the plunger rod 210. In other instances, the distance C may be greater or less than the height H3 of the distal end portion 211 of the plunger rod 210. The flexible wall portion 162 and contoured ramp 180 are discussed in more detail below. In some implementations, the flexible wall portion 162 may be omitted. For example, in some implementations, the flexible wall portion may be unnecessary, as the plunger 30 and the associated plunger rod 210 maintain are configured such that a plunger tip, e.g., plunger tip 220 discussed in more detail below, remains in contact with the contoured ramp 180 during advancement of the plunger 30.

As also shown in FIG. 7, the injector body 20 may include a contoured surface 192 that is offset from the receiving surface 190. A wall 194 is formed adjacent to the contoured surface 192. A freely extending end 452 of a haptic 450, shown in FIG. 17, contacts the contoured surface 192 when IOL 70 is received into the compartment 80.

Figure 8:
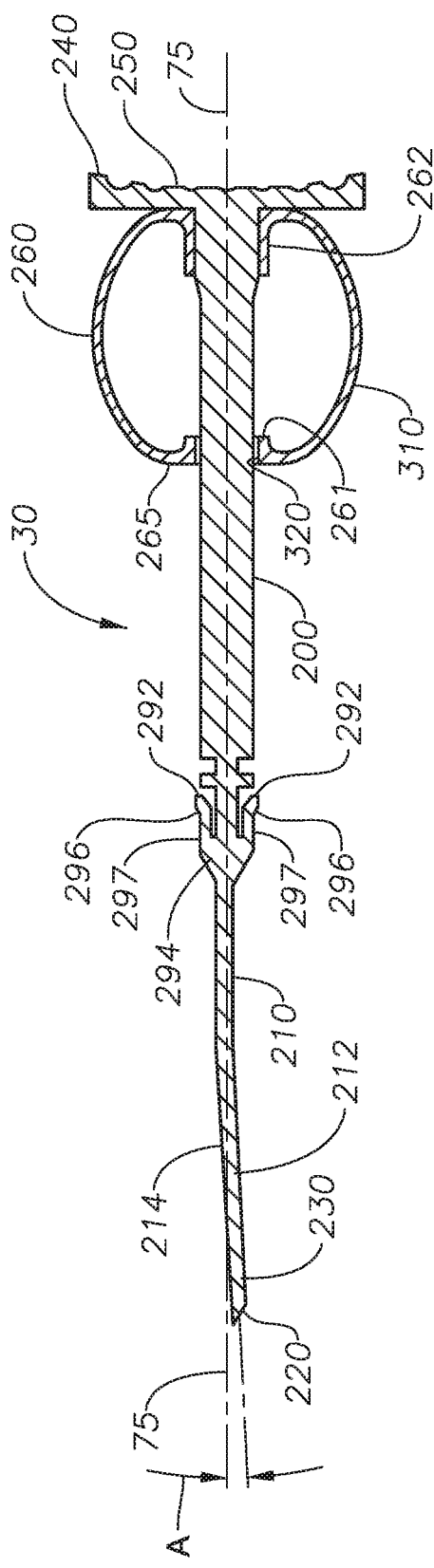
FIG. 8 is a cross-sectional view of a plunger.
Figure 9:
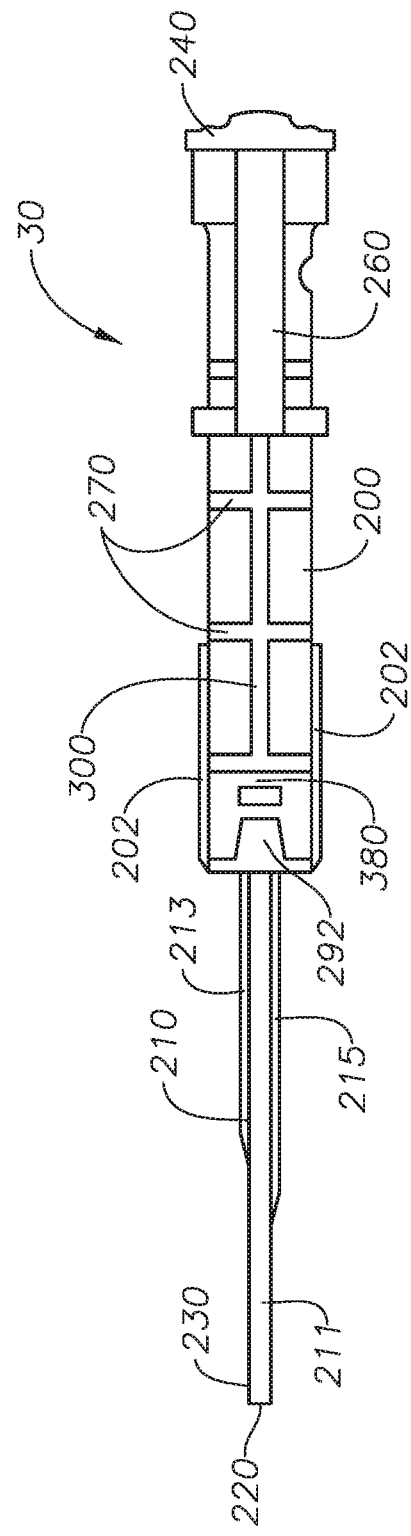
FIG. 9 is a bottom view of a plunger.

Referring to FIGS. 1 and 8-9, the plunger 30 may include a body portion 200, a plunger rod 210 extending distally from the body portion 200, and a plunger tip 220 formed at a distal end 230 of the plunger rod 210. The plunger 30 may also include a flange 240 formed at a proximal end 250 of the body portion 200. A biasing element 260 may be disposed on the plunger 30. In some instances, the biasing element 260 may be a spring. In some implementations, the biasing element 260 may be disposed adjacent to the flange 240. A proximal end 262 may be fixedly attached at the body portion adjacent to the flange 240. In other instances, the biasing element 260 may be disposed at another location along the body portion 200. In still other implementations, the biasing element 260 may be formed or otherwise disposed on the injector body 20 and adapted to engage the plunger 30 at a selected location during advancement of the plunger 30 through bore 40. Still further, in other implementations, the biasing element 260 may be omitted.

The flange 240 may be used in concert with the tabs 110 to advance the plunger 30 through the injector housing 20. For example, a user may apply pressure to tabs 110 with two fingers while applying opposing pressure to the flange 240 with the user's thumb. A surface of the flange 240 may be textured in order to provide positive gripping by a user. In some instances, the texture may be in the form of a plurality of grooves. However, any desired texture may be utilized.

The body portion 200 may include a plurality of transversely arranged ribs 270. In some instances, the ribs 270 may be formed on both a first surface 280 and a second surface 290 of the body portion 200, shown in FIG. 1. In other instances, the ribs 270 may be formed on only one of the first surface 280 and second surface 290. A longitudinally extending rib 300 may also be formed on one or both of the first and second surfaces 280, 290.

In some instances, the body portion 200 may also include one or more protrusions 202, as shown in FIG. 9. The protrusions 202 may extend longitudinally along a length of the body portion 200. The protrusions 202 may be received grooves 204 formed in the injector body 20, as shown in FIG. 1. The protrusions 202 and grooves 204 interact to align the plunger 30 within the bore 40 of the injector body 20.

The body portion 220 may also include cantilevered members 292. The cantilevered members 292 may extend from a distal end 294 of the body portion 200 towards the proximal end 250. The cantilevered members 292 may include flared portions 296. The cantilevered members 292 may also include substantially horizontal portions 297. The flared portions 296 are configured to engage the interior wall 298 of the injector body 20 that defines the bore 40, as shown in FIG. 2. Engagement between the cantilevered members 292 and the interior wall 298 generates a force resistive to advancement of the plunger 30 and provides a tactile feedback to the user during advancement of the plunger 30. For example, in some implementations, the resistive force generated by contact between the cantilevered members 292 and the interior wall 298 may provide a baseline resistance that resists advancement of the plunger 30.

In some instances, the plunger rod 210 may include an angled portion 212. The distal end portion 211 may form part of the angled portion 212. The angled portion 212 may define an angle, A, within the range of 1° to 5° with the longitudinal axis 75. In some instances, the angle A maybe 2°. In some instances, the angle A may be 2.5°. In still other instances, the angle A may be 3°, 3.5°, 4°, 4.5°, or 5°. Further, while the above values of A are provided as examples, the angle A may be greater or less than the indicated range or any value in between. Thus, the angle A may be any desired angle.

The angled portion 212 ensures that the plunger tip 220 contacts and follows the receiving surface 190 as the plunger 30 is advanced through the bore 40. Particularly, the angle A defined by the angled portion 212 exceeds what is needed to cause the plunger tip 220 to contact the interior wall 298 of the bore 40. That is, when the plunger 30 is disposed within the bore 40, engagement between the plunger tip 220 and the interior wall 298 causes the angled portion 212 to bend inwardly due to the angle A. Consequently, the angled portion 212 ensures that the plunger tip 220 properly engages the haptics and optic of an IOL being inserted from the IOL injector 10. This is described in greater detail below. Although the angled portion 212 is shown as being a substantially straight portion bent at an angle relative to the remainder of the plunger rod 210, the scope is not so limited. In some instances, a portion of plunger rod 210 may have a continuous curvature. In other instances, an entire length of the plunger rod 210 may be bent or have a curvature. Further, the amount of angular offset from the longitudinal axis 75 or amount of curvature may be selected in order to provide a desired amount of engagement between the plunger tip 220 and the interior surfaces of the injector body 20.

The biasing element 260 may be affixed to the body portion 200 adjacent to the flange 240. In some instances, the biasing element 260 may form a hoop 310 extending distally along the body portion 200 that functions as a spring to resist advancement of the plunger 30 when the hoop 310 engages the injector body 20. The biasing element 260 may also include a collar 261 that defines a channel 320 through which the body portion 200 extends. Thus, in operation, as the plunger 30 is advanced through the bore 40 of the injector body 20 (i.e., in the direction of arrow 330 shown in FIG. 2), a distal end 265 of the biasing element 260 contacts the proximal end 50 of the injector body 20 at a selected location along the stroke of the plunger 30. As the injector 30 is further advanced, the biasing element 260 is compressed and the channel 320 permits the distal end 265 of the biasing element 260 to move relative to the body portion 200. Similarly, the channel 320 permits relative movement between the body portion 200 and the distal end 265 of the biasing element 260 during proximal movement of the plunger 30 (i.e., in the direction of arrow 340, also shown in FIG. 2).

Figure 10:
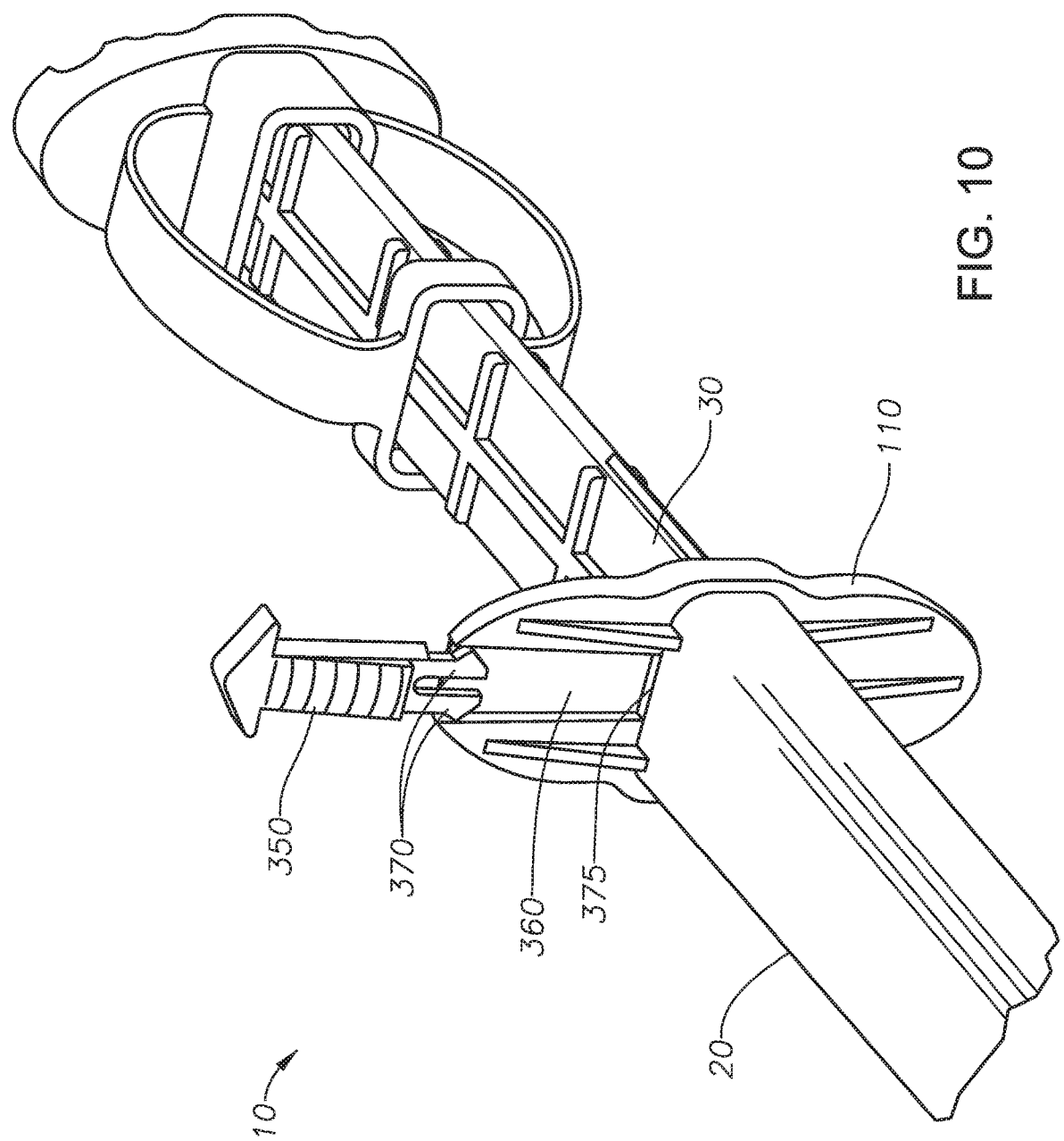
FIG. 10 is a partial perspective view showing tabs and a plunger lock of an example intraocular lens injector.

Referring to FIGS. 2, 9, and 10, the IOL injector 10 may also include a plunger lock 350. The plunger lock 350 is removably disposed in a groove 360 formed in one of the tabs 110. The plunger lock 350 includes a protrusion 370 formed at one end thereof. The plunger lock 350 may include a single protrusion 370, as shown in FIG. 2. In other instances, the plunger lock 350 may include a plurality of protrusions 370. For example, FIG. 10 illustrates an example plunger lock 350 having two protrusions 370. In other instances, the plunger lock 350 may include additional protrusions 370.

When installed, the protrusion 370 extends through an aperture 375 formed in the injector body 20 and is received into a slot 380 formed in the plunger 30. When the plunger lock 350 is installed, the protrusion 370 and slot 380 interlock to prevent the plunger 30 from moving within the bore 40. That is, the installed plunger lock 350 prevents the plunger 30 from being advanced through or removed from the bore 40. Upon removal of the plunger lock 350, the plunger 30 may be freely advanced through the bore 40. In some instances, the plunger lock 350 may include a plurality of raised ribs 390. The ribs 390 provide a tactile resistance to aid in removal from and insertion into groove 360.

The plunger lock 350 may be U-shaped and define a channel 382. The channel 382 receives a portion of the tab 110. Further, when fitted onto the tab 110, a proximal portion 384 of the plunger lock 350 may be outwardly flexed. Consequently, the plunger lock 350 may be frictionally retained on the tab 110.

Referring to FIGS. 2 and 8, in some implementations, the body portion 20 may include shoulders 392 formed in bore 40. The shoulders 392 may be formed at a location in the bore 40 where the bore 40 narrows from an enlarged proximal portion 394 and a narrower distal portion 396. In some instances, the shoulder 392 may be a curved surface. In other instances, the shoulder 392 may be defined a stepped change in the size of bore 40.

The cantilevered members 292 may engage the shoulder 392. In some implementations, the flared portion 296 of the cantilevered members 292 may engage the shoulder 392. In some instances, a location at which the cantilevered members 292 engage the shoulder 392 may be one in which the slot 380 aligns with the aperture 375. Thus, in some implementations, engagement between the cantilevered members 292 and shoulder 392 may provide a convenient arrangement for insertion of the plunger lock 350 to lock the plunger 30 in place relative to the injector body 20. In other implementations, the slot 380 and the aperture 375 may not align when the cantilevered members 292 engage the shoulder 392.

As the plunger 30 is advanced through the bore 40, the flared portion 296 of the cantilevered members 292 may be inwardly displaced to comply with the narrowed distal portion 396 of the bore 40. As a result of this deflection of the flared portion 296, the cantilevered members 292 apply an increased normal force to the interior wall 298 of the bore 40. This increased normal force generates a frictional force that resists advancement of the plunger 30 through bore 40, thereby providing tactile feedback to the user.

Figure 17:
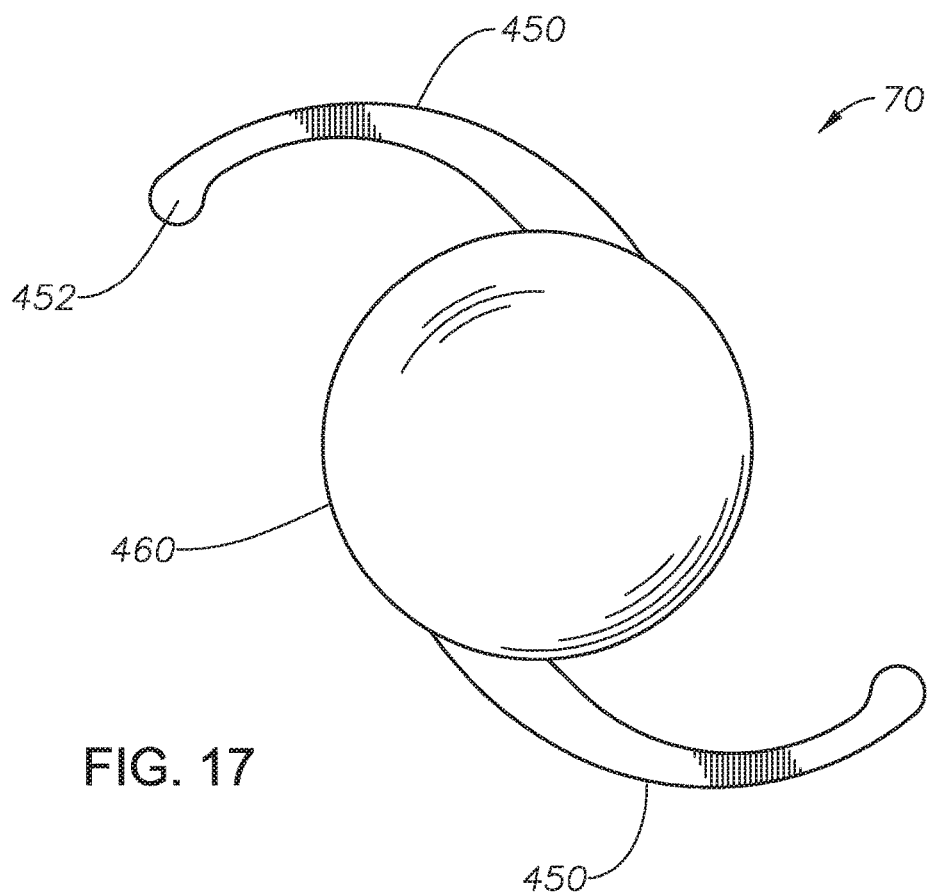
FIG. 17 shows an example IOL.

Referring to FIGS. 1 and 2, the IOL injector may also include an IOL stop 400. The IOL stop 400 is received into a recess 410 formed in an outer surface 420 the door 90. The IOL stop 400 may include a protrusion 430 that extends through an opening 440 formed in the door. The protrusion 430 extends between a haptic and optic of an IOL loaded into the compartment 80. As shown in FIGS. 1 and 17, the IOL 70 includes haptics 450 and an optic 460. The protrusion 430 is disposed between one of the haptics 450 and the optic 460. The IOL stop 430 may also include a tab 435. The tab 435 may be gripped by a user for removal of the IOL stop 430 from the injector body 20.

The IOL stop 400 may also include an aperture 470. The aperture 470 aligns with another opening formed in the door 90, for example opening 472 shown in FIG. 13. The aperture 470 and second opening 472 in the door 90 form a passageway through which a material, such as a viscoelastic material, may be introduced into the compartment 80.

The IOL stop 400 is removable from the door 90. When installed, the IOL stop 400 prevents advancement of the IOL, such as IOL 70. Particularly, if advancement of the IOL 70 is attempted, the optic 460 contacts the protrusion 430, thereby preventing advancement of the IOL 70.

Figure 11:
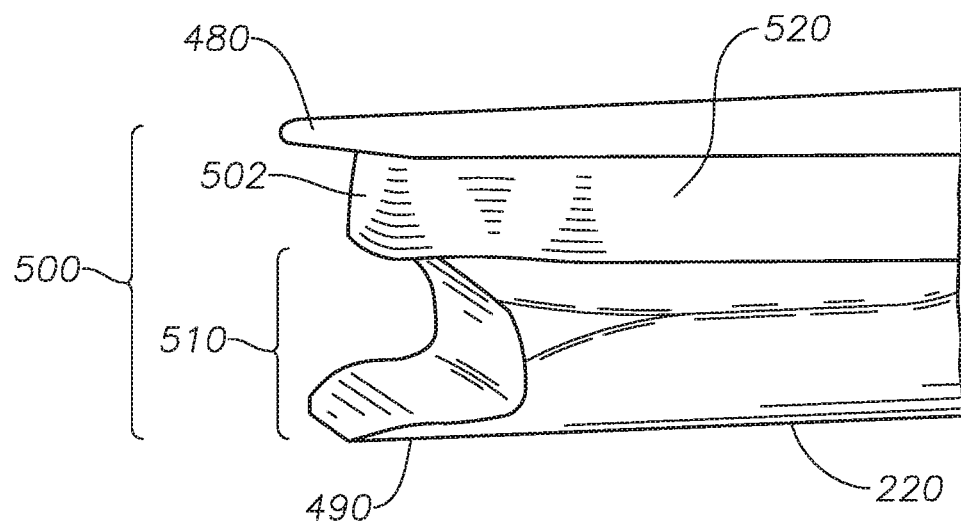
FIG. 11 is a detail view of an example plunger tip of plunger.

FIG. 11 shows an example plunger tip 220. The plunger tip 220 may include a first protrusion 480 and a second protrusion 490 extending from opposing sides. The first and second protrusions 480, 490 define a first groove 500. The first groove 500 defines a surface 502. A second groove 510 is formed within the first groove 500. The first groove 500, particularly in combination with the first protrusion 480, serves to capture and fold a trailing haptic of an IOL. The second groove 510 functions to capture and fold an optic of an IOL.

A side wall 520 of the plunger tip 220 may be tapered. The tapered side wall 520 may provide a nesting space for a gusseted portion of the trailing haptic of an IOL. The gusseted portion of the haptic tends to remain proximal to the IOL optic. Thus, the tapered side wall 520 may provide a nesting space that promotes proper folding of the IOL during delivery into an eye.

Figure 18:
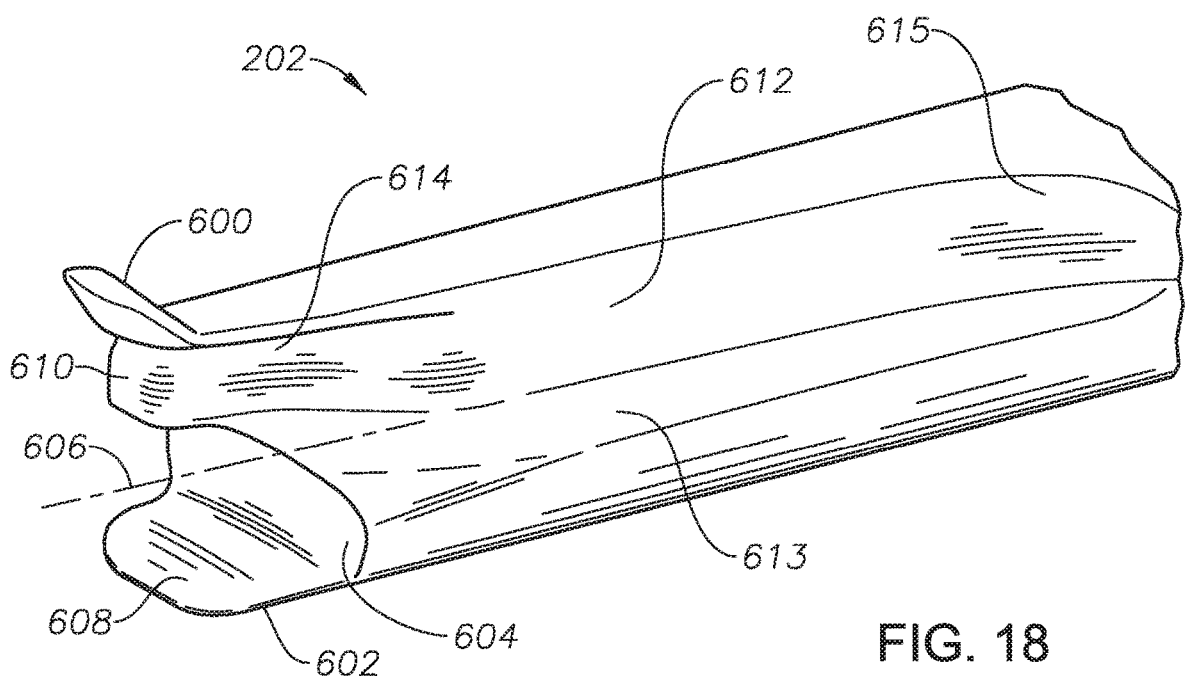
FIG. 18 is a perspective view of an example plunger tip.
Figure 19:
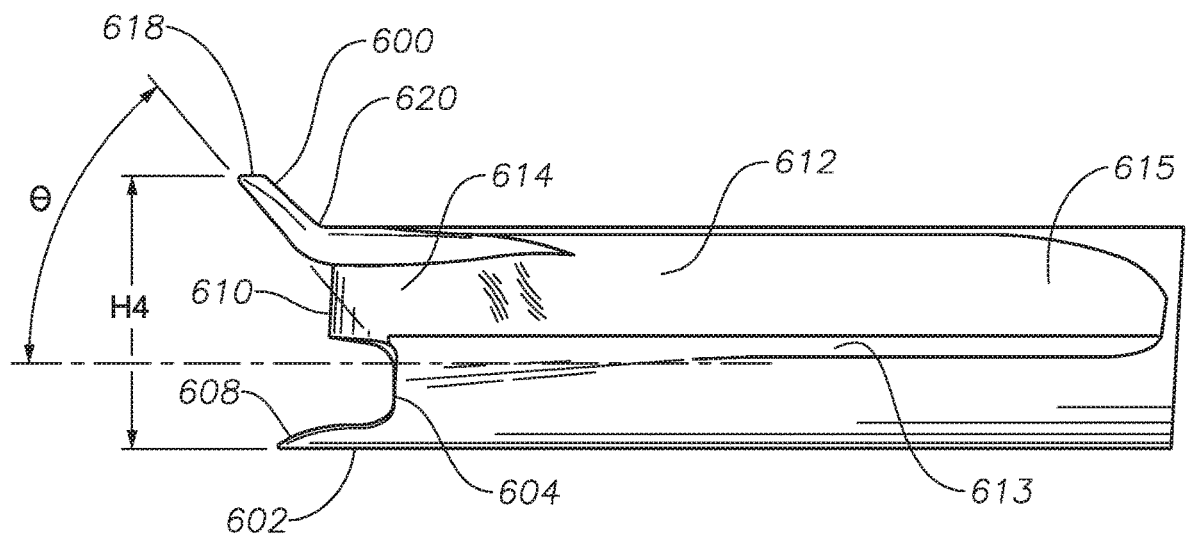
FIG. 19 is a side view of the example plunger tip of FIG. 18.
Figure 20:
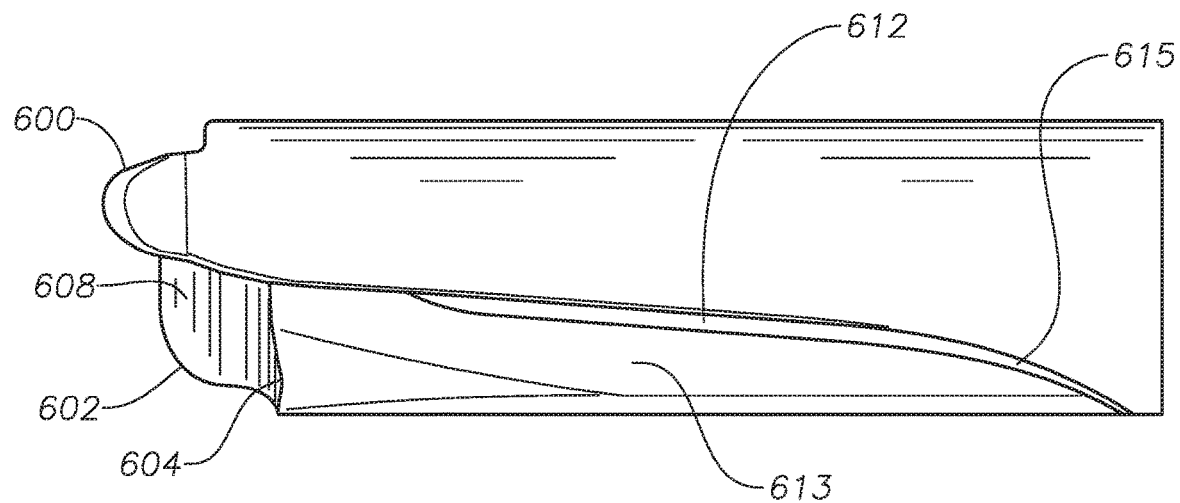
FIG. 20 is a top view of the example plunger tip of FIG. 18.

FIGS. 18-20 show another example plunger tip 220. This plunger tip 220 includes a first protrusion 600, a second protrusion 602, and a groove 604. The first protrusion extends at an oblique angle θ from longitudinal axis 606. In some instances, the angle θ may be between 25° to 60°. In other instances, the angle θ may be lower than 25° or larger than 60°. In other instances, the angle θ may be between 0° to 60°. In still other implementations, the angle θ may be between 0° and 70°; 0° and 80°; or 0° and 90°. Generally, the angle θ may be selected to be any desired angle. For example, the angle θ may selected based on one or more of the following: (1) a size, such as a height, of passage 64 formed within the nozzle 60; (2) the height of the compartment 80; (3) how the height of the passage 64 and/or compartment varies along their respective lengths; and (3) the thickness of the plunger tip 220. The second protrusion 602 may include a tapered portion 608. The tapered portion 608 is operable to engage an optic of an IOL, such as optic 460 shown in FIG. 17. The optic may slide along the tapered surface so that the optic may be moved into the groove 604. As a result, the second protrusion 602 is positioned adjacent to a surface of the optic.

The example plunger tip 220 shown in FIGS. 18-20 also include a surface 610 that may be similar to the surface 502. The surface 610 is adapted to contact and displace a trailing or proximally extending haptic, such as haptic 450 shown in FIG. 17, so that the haptic folds. In some instance, the surface 610 may be a flat surface. In other instances, the surface 610 may be a curved or otherwise contoured surface. The example plunger tip 220 may also include a side wall 612 and support surface 613. Similar to the side wall 520, the side wall 612 may be tapered, as shown in FIG. 20. In some instances, the side wall 612 may include a first curved portion 614. The first curved portion 614 may receive a bent portion of the trailing haptic that remains proximal to the optic during folding. The trailing haptic is supported by support surface 613 during the folding process. The side wall 612 may also include a second curved surface 615.

The obliquely-extending first protrusion 600 effectively increases a height H4, as compared to the plunger tip 220 shown in FIG. 11, for example. This increased height H4 improves the ability of the plunger tip 220 to capture the trailing haptic during advancement of the plunger 30. In operation, as the plunger 30 is advanced distally, the distal end 618 engages an interior wall of the delivery passage 127 due to changes in the height H1 of the delivery passage 127. As the height H1 decreases, the first protrusion 600 pivots about hinge 620, effectively reducing the total height H4 of the plunger tip 220. As the first protrusion 600 pivots about hinge 620 and rotated in a direction towards the second protrusion 602, the first protrusion 600 captures the trailing haptic between the optic of the IOL and the first protrusion 600. Therefore, with the first protrusion 600 pivotable about the hinge 620, the size of the plunger tip 220 is able to adapt and conform to the changing height H1 of the delivery passage 127 as the IOL is advanced distally and folded.

Figure 12:
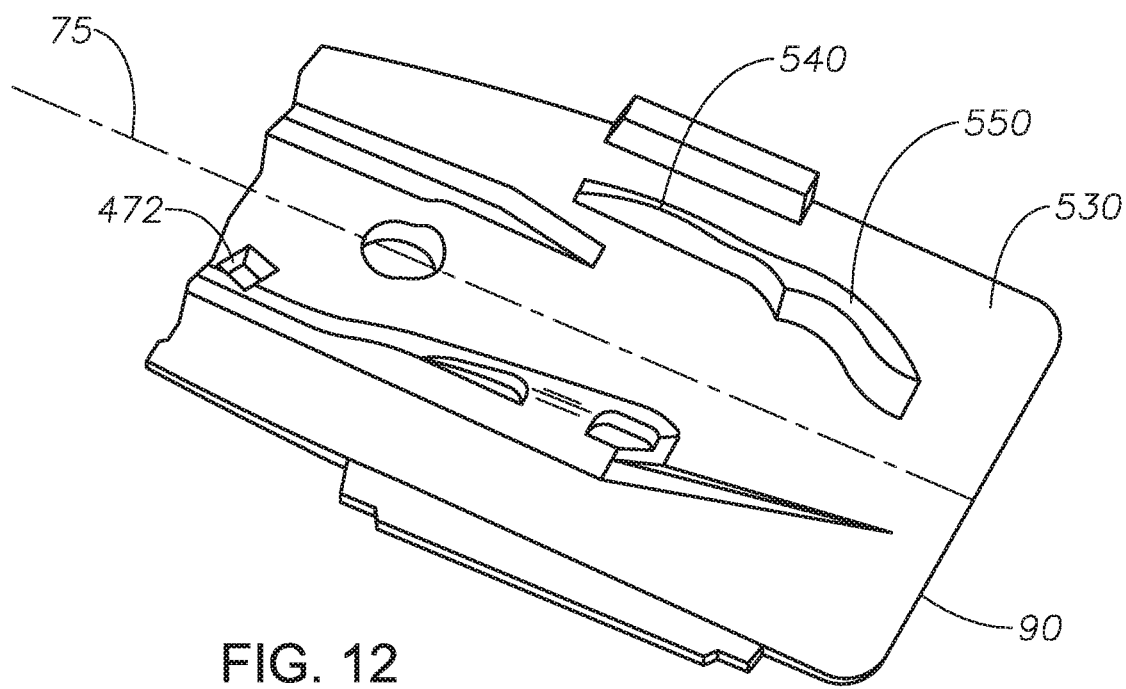
FIG. 12 shows an example interior surface of a door enclosing a lens-receiving compartment of an intraocular lens injector.

FIG. 12 shows an interior surface 530 of door 90. The surface 510 may include a ridge 530. The ridge 530 may include a curved portion 540. In the example illustrated, the curved portion 540 extends proximally and inwardly towards the longitudinal axis 75. The curved portion 540 is configured to overlay a portion of a trailing haptic of an IOL, which promotes proper folding of the IOL when the plunger 30 is advanced through the injector body 20.

In operation, the plunger lock 350 may be inserted into the groove 360 to lock the plunger 30 in position relative to the injector body 20. An IOL, such as IOL 70, may be loaded into the compartment 80. For example, the door 90 may be opened by a user and a desired IOL inserted into the compartment 80. The door 90 may be closed upon insertion of the IOL into the compartment 80. In some instances, an IOL may be preloaded during manufacturing.

The IOL stop 400 may be inserted into the recess 410 formed in the door 90. Viscoelastic material may be introduced into the compartment 80 via the aligned aperture 470 and corresponding opening formed in the door 90. The viscoelastic material functions as a lubricant to promote advancement and folding of the IOL during advancement and delivery of the IOL into an eye. In some instances, the viscoelastic material may be introduced into the compartment 80 at the time of manufacturing.

The IOL stop 400 may be removed from the recess 410 formed in the door 90, and the plunger lock 350 may be removed from the groove 360. The plunger 30 may be advance through the bore 40. Sliding engagement between the cantilevered members 292 and the interior wall 298 of the injector body 20 generates a resistive force that resists advancement of plunger 30. In some instances, the plunger 30 may be advanced through the bore 40 until the plunger tip 220 extends into the compartment 80. For example, the plunger 30 may be advanced until the plunger tip 220 is adjacent to or in contact with the IOL. In other instances, the plunger 30 may be advanced through the bore 40 such that the IOL is partially or fully folded. Further, the plunger 30 may advance the IOL to a position within the nozzle just short of being ejected from the distal opening 125. For example, in some instances, advancement of the plunger 30, prior to insertion of the nozzle 120 into a wound formed in the eye, may be stopped at the point where the distal end 265 of the biasing element 260 contacts the proximal end 50 of the injector body 20.

Figure 21:
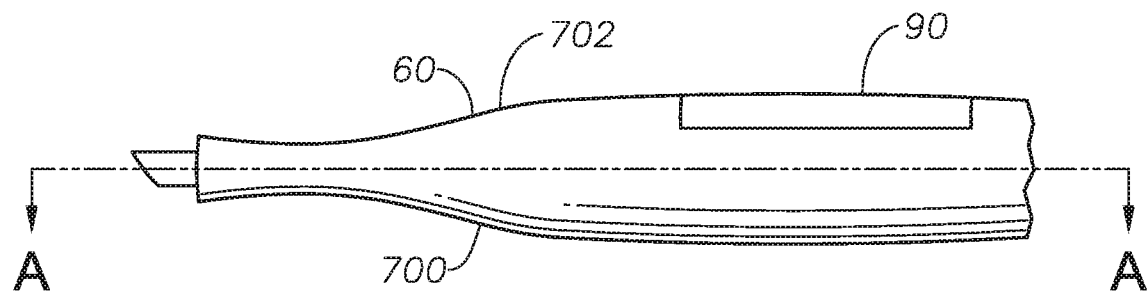
FIG. 21 is a side view of a distal end portion of an example IOL injector.
Figure 22:
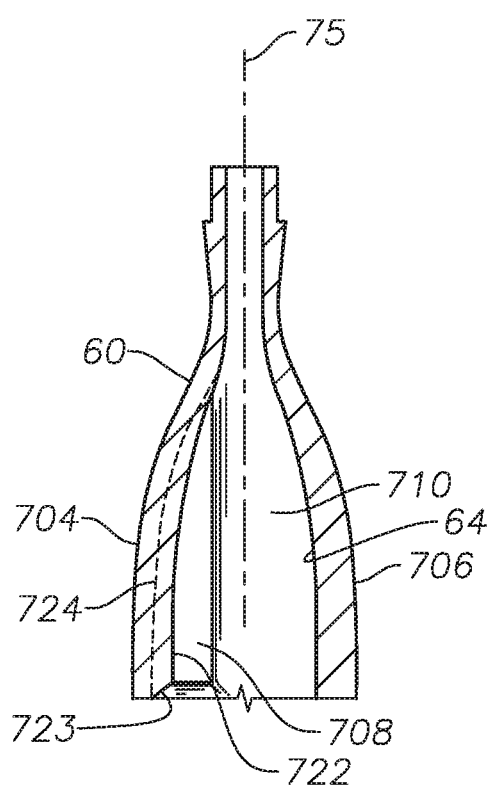
FIG. 22 is a cross-sectional view taken along line A-A of FIG. 21.

FIG. 21 shows the distal end portion 60 of the IOL injector 10. FIG. 22 is a cross-sectional view of the distal end portion 60 of the IOL injector 10 taken along line A-A. Longitudinal axis 75 is shown in FIG. 22 and extends centrally along the passage 64 such that the longitudinal axis 75 divides the distal end portion 60 symmetrically in FIG. 22. Referring to FIGS. 21 and 22, the distal end portion 60 includes a first sidewall 700, a second sidewall 702 opposite the first sidewall 700, a third sidewall 704 disposed between the first and second sidewalls 700 and 702, and a fourth sidewall 706 opposite the third sidewall 704 and also disposed between the first and second sidewalls 700 and 702. The sidewalls 700, 702, 704, and 706 define the passage 64.

Figure 23:
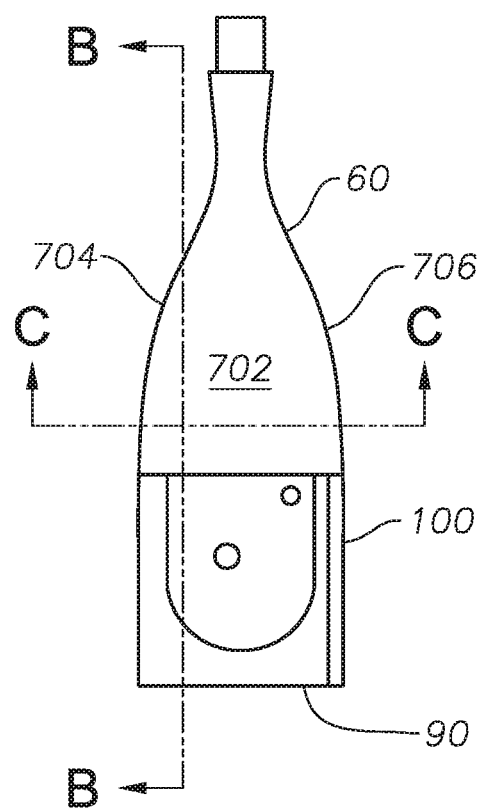
FIG. 23 is a plan view of the distal end portion of the IOL injector of FIG. 21.
Figure 28:
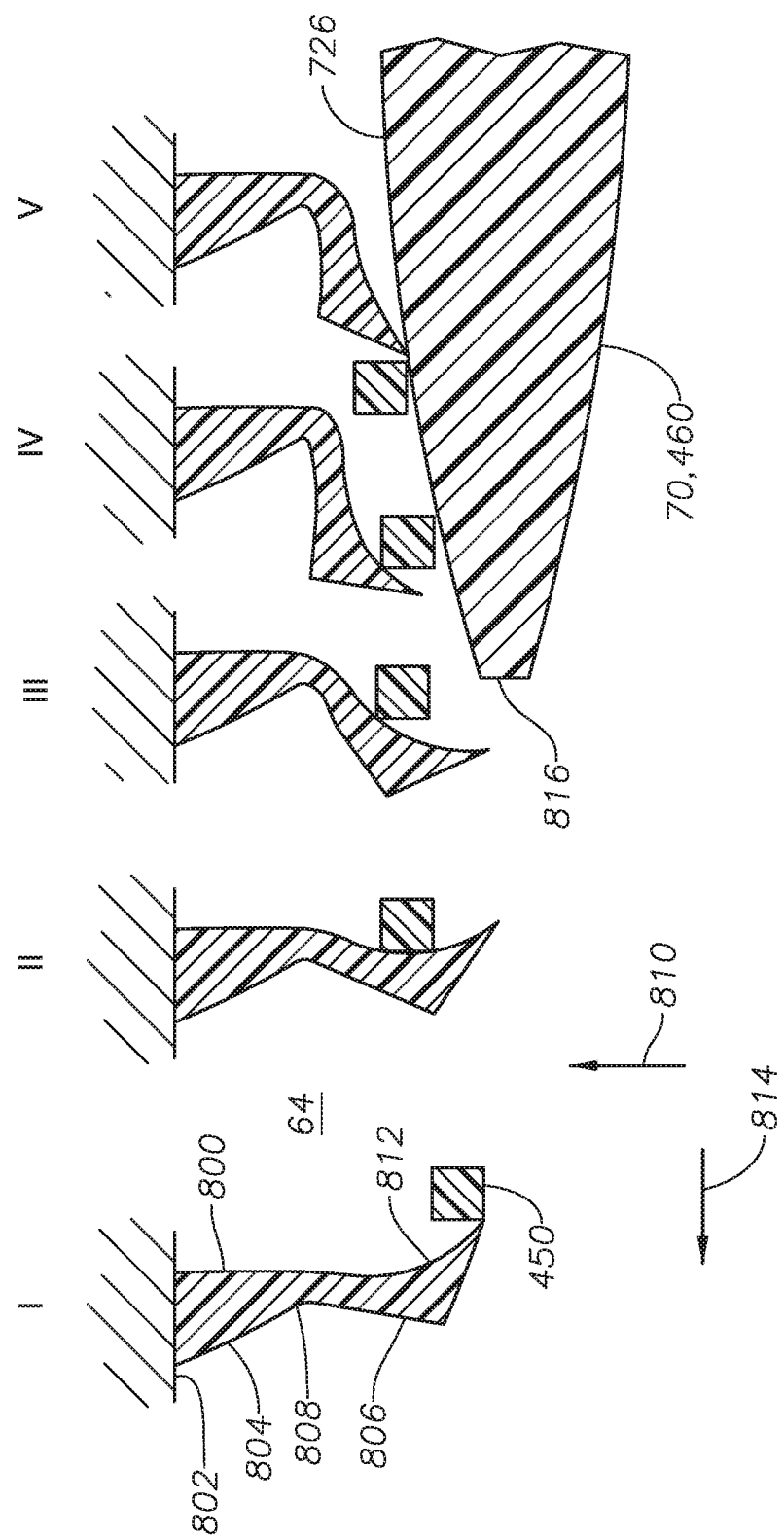
FIG. 28 shows an example lifting feature disposed within an interior passage of an IOL injector operable to lift a leading haptic of an IOL during advancement of the IOL.

In order to provide improved folding of an IOL, such as IOL 70, a ramp 708 is formed on an interior surface 710 of the first sidewall 700. Referring to FIGS. 22, 23, and 28, the ramp 708 includes a peak 709, a leading surface 712 disposed proximally the peak 709, and a trailing surface 713 disposed distally of the peak 709. The peak 709 extends along a width of the ramp 708 and separates the leading surface 712 from the trailing surface 713. The peak 709 represent a portion of the ramp 708 with the largest separation from plane C, shown in FIG. 24 and discussed in more detail below. As is readily apparent, the leading surface 712 of the ramp 708 increases the lift, i.e., displacement in the direction of arrow 709, of a leading haptic of an IOL (e.g., a leading haptic 450 of IOL 70, shown in FIG. 10) at a much faster rate as the IOL is advance through the passage 64 than would otherwise be provided by the surface 710 if the ramp 708 were omitted. The ramp 708 operates to mitigate or eliminate improper folding of the leading haptic during folding of the IOL within the IOL injector 10. For example, the ramp 708 may avoid improper folding in which the leading haptic remains distal to an in contact with a leading edge 728 (shown in FIG. 24) of the optic 460 during folding of the IOL 70. Thus, the ramp 708 is operable to lift the leading haptic 450 above the optic 460 such that the haptic 450 is able to be folded over the optic 460 as the IOL 70 is folded prior to being expelled from the IOL injector 10 and into an eye for implantation.

As shown in FIG. 22, the ramp 708 is laterally offset from the longitudinal axis 75, which forms a centerline along the IOL injector 10, towards the third sidewall 704. The location of the ramp 708 is such that a freely extending end of a leading haptic of an IOL, such as freely extending end 452 of haptic 450 of IOL 70 extending digitally from the optic 460, encounters the ramp 708 as the IOL is advance along the delivery passage 127 by the plunger 30.

Figure 24:
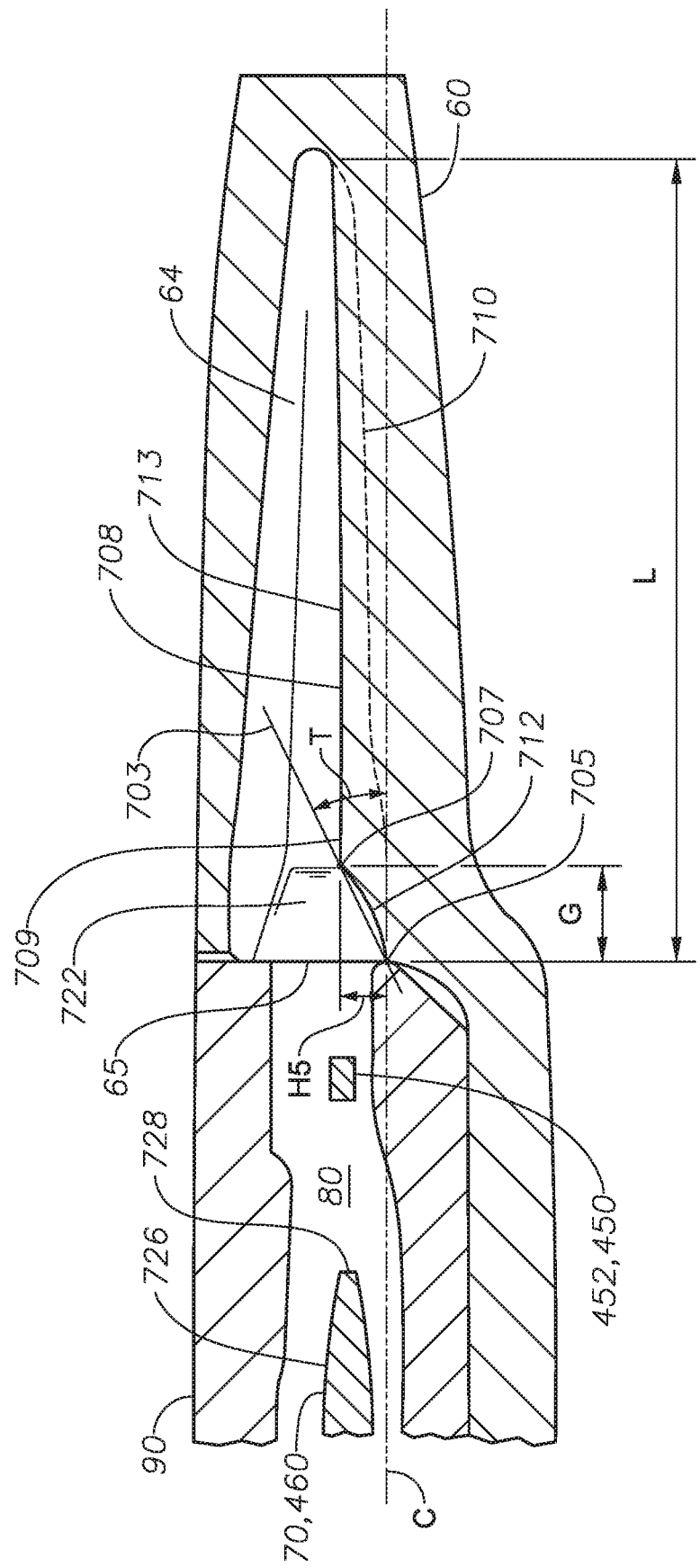
FIG. 24 is a cross-sectional view taken along line B-B of FIG. 23.

FIG. 23 is a plan view of the distal end portion 60 of the IOL injector 10 showing the second sidewall 702. FIG. 24 is a cross-sectional view of the distal end portion 60 taken along line B-B shown in FIG. 22. The line B-B represents a plane passing through a portion of the ramp 708 having the largest distance between a point along the peak 709 and the plane C, shown in FIG. 24. H5 represents the maximum dimension between the ramp 708 and the plane C. The ramp 708 is positioned within the passage 64 to contact and engage the freely extending end of the leading haptic. In the illustrated example, the ramp 708 is disposed distally of the threshold 65 between the compartment 80 and the passage 64. The ramp 708 begins at a proximal end indicated by point 705. In some instances, a longitudinal distance G between the point 705 and the peak 709 (which, in some instances, may be coincident with point 707, described in more detail below) may be within the range of 0.5 mm to 1.5 mm. Thus, in some implementations, the distance G may be 0.5 mm, 0.6 mm, 0.7 mm, 0.8 mm, 0.9 mm, 1.0 mm, 1.1 mm, 1.2 mm, 1.3 mm, 1.4 mm, or 1.5 mm. However, the distance G may be selected to be any value within the indicated range or a value larger or smaller than the indicated range. Line 710 corresponds to an interior surface of the first sidewall 700 defining the passage 64 away from and not forming part of the ramp 708. A length L of the ramp 708 along the cross-section shown in FIG. 24 may be within the range of 8 mm to 10 mm. In other implementations, the length L of the ramp 708 may be greater than 10 mm or less than 8 mm.

Referring to FIGS. 30-33 illustrates the operation of the ramp 708 in lifting the leading haptic 450 above optic 460 as the IOL 70 is advanced within the IOL injector 10. In operation, as the plunger rod 210 advances the IOL 70 along the delivery passage 127, the freely extending end 452 of the leading haptic 450 contacts and rides along a leading surface 712 of the ramp 708. As the IOL 70 is continued to be advanced, the leading haptic 450 is lifted as it rides along the leading surface 712. Lifting of the leading haptic 450 continues until the leading haptic 450 has obtained a sufficient height above the optic 460 of the IOL. For example, a height obtained by the leading haptic 450 as a result of riding along the leading surface 712 of the ramp 708 may be selected to ensure that leading haptic avoids being trapped forward or distal of a leading edge 714 of the optic 460. Further, a position of the leading surface 712 of the ramp 708 longitudinally along the distal end portion 60 and a slope of the leading surface 712 may be selected such that the leading haptic 450 achieves a desired height above the optic 460 before or simultaneous with curling of the lateral edges 453 (shown in FIG. 14) of the optic 460 as the optic 460 begins to fold. A ramp 708 configured in such a way ensures that the freely extending end 452 of the leading haptic 450 is tucked proximal to the leading edge 714 of the optic and between the folded lateral sides 453 thereof. An illustration of this folding arrangement of the leading haptic relative to the optic is shown in FIG. 19.

Figure 25:
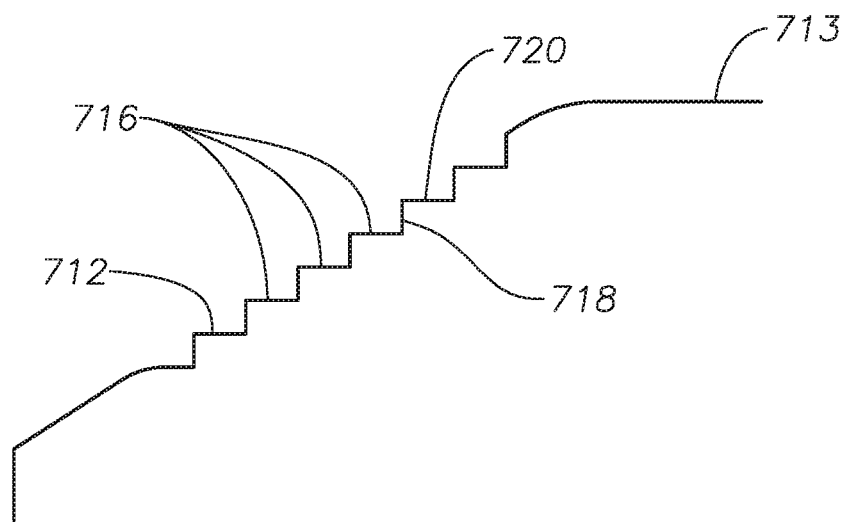
FIG. 25 is a detail view of a ramp formed in an interior passage of a distal end portion of an IOL injector.

In the example shown in FIG. 24, the leading surface 712 is a smooth surface. That is, in some implementations, the leading surface 712 may be free of discontinuities or rapid changes in curvature. However, the scope of the disclosure is not so limited. In some implementations, the leading surface 712 of the ramp 708 may have stepped surface. FIG. 25 shows a detail cross-sectional view of an example leading surface 712 of the ramp 708 in which the leading surface 712 includes a plurality of steps 716. In some instances, leading surface 712 may be formed entirely of steps 716. In other instances, the leading surface 720 may have a plurality of steps along only a portion of its length. In other implementations, the sizes of one or more steps 716 may vary from the sizes of one or more other steps 716 of the leading surface 712.

In some implementations, each of the steps 716 includes a rise 718 and a run 720. The run 720 extends in a direction parallel to a longitudinal axis 75 of the IOL injector 10, while the rise 718 extends in a direction perpendicular to the longitudinal axis 75 of the IOL injector 10. In some implementations, the rise 718 of one or more of the steps 716 may have a length in the range of 0.2 to 0.5 mm. Particularly, the length of the rise 718 may be 0.2 mm, 0.3 mm, 0.4 mm, or 0.5 mm. However, these dimensions are merely examples. In other implementations, the length of the rise 718 may be larger or smaller than the indicated range. That is, in some instances, the rise 718 may be larger than 0.5 mm or smaller than 0.2 mm.

The run 720 of one or more of the steps 716 may have a length in the range of 0.2 to 0.5 mm. Particularly, the length of the run 720 may be 0.2 mm, 0.3 mm, 0.4 mm, or 0.5 mm. However, these dimensions are merely examples. In other implementations, the length of the run 720 may be larger or smaller than the indicated range. That is, in some instances, the run 720 may be larger than 0.5 mm or smaller than 0.2 mm.

Although FIG. 25 shows an example leading surface 712 having a plurality of steps 716 that are uniform in size. Thus, in some implementations, with the leading surface 712 having a plurality of steps 716 with uniform sizes, the leading surface 712 defines a linear slope. However, the scope of the disclosure is not so limited. Rather, in other instances, one or more of the rise 718, the run 720, or both the rise 718 and run 720 of one or more of the steps 716 may be different than one or more other steps 716. In some instance, the run 718 of the steps may decrease in the distal direction along the leading surface 712. In other implementations, the run 718 of the steps may increase in the distal direction along the leading surface 712. In some instances, the rise 718 of the steps may increase in the distal direction along the leading surface 712. In other implementations, the rise 718 of the steps may decrease in the distal direction along the leading surface 712. In instances where the rise 718 and run 720 of one or more of the steps 716 varies, the leading surface 712 may define an overall curved surface or, more generally, a non-linear surface. In some implementations, the stepped leading surface 712 may be arranged to form an overall parabolic shape to the leading surface 712. An overall parabolic shape of the leading surface 712 may alter an amount of lift imparted to the leading haptic 450 as a distance traveled by the leading haptic 450 in the distal direction changes. Particularly, the amount of lift imparted to the leading haptic 450 may increase per rate of movement of the leading haptic 450 in the distal direction along the longitudinal axis of the passage 64 of the distal end portion 60. However, the overall shape defined by the leading surface 712 may be any desired shape. For example, the leading surface 712 may have an inclined undulating surface, an inclined flat surface, or any other desired surface.

An overall slope of the ramp 708 is defined by a line 703 extending from a point 705, a proximal end of the ramp 708, to a point 707 wherein the line 705 tangentially touches the peak 709 of the ramp 708. The slope line 703 is angularly offset from the plane C by an angle T. In some instances, the angle T may be between 17° and 27°. Particularly, in some instances, the angle T may be 17°, 18°, 19°, 20°, 21°, 22°, 23°, 24°, 25°, 26°, or 27°. However, the angle T may be selected to be any value within the indicated range or a value larger or smaller than the indicated range.

Referring to FIGS. 22, 24, and 25, the trailing surface 713 of the ramp 708 gradually recedes into the interior surface 710 of the first sidewall 700. In the example shown in FIG. 24, the trailing surface 713 has a positive slope as the trailing surface 713 extends distally. In some examples, the positive slope of the trailing surface 713 is provided for manufacturability of the IOL injector 10 and, particularly, for the distal end portion 60. In the case of injection molding, for example, a positive slope of the trailing surface 713 provides a draft angle that facilitates manufacturing of the distal end portion 60. However, the trailing surface 713 need not have a positive slope. In other implementations, the trailing surface 713 may have a neutral slope, i.e., a slope of zero, or a negative slope. In still other implementations, the trailing surface 713 of the ramp 708 may be omitted.

In some implementations, the third sidewall 704 may also include ramp 722 formed on an interior surface thereof, as shown in FIG. 22. In some instances, the ramp 722 may blend with the ramp 708. For example, in some instances, the ramp 722 may be a continuation of the ramp 708 that continues from the inner surface of the first sidewall 700 onto the inner surface of the third sidewall 704. In some implementations, the ramp 722 may be omitted.

Figure 26:
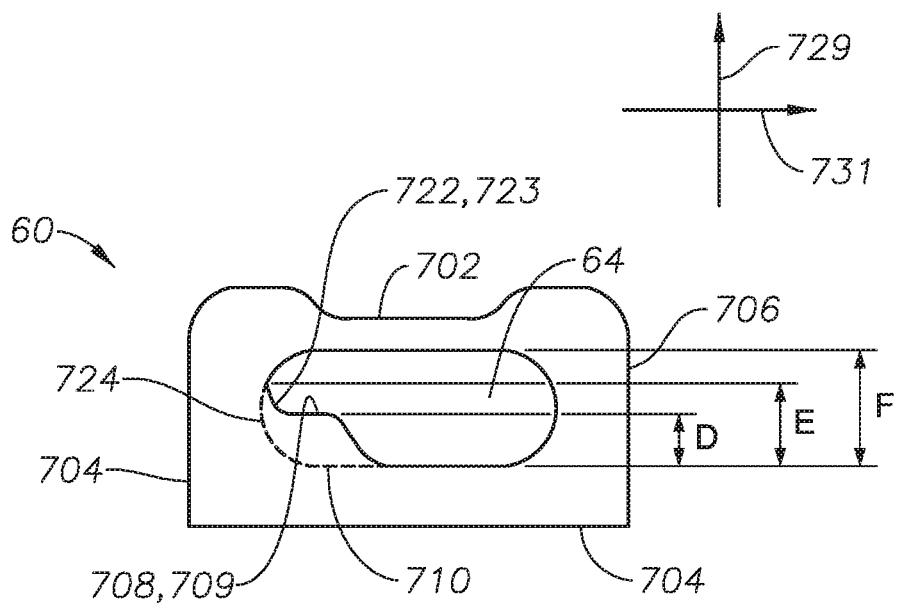
FIG. 26 is a cross-sectional view taken along line C-C of FIG. 23.

The ramp 722 includes a leading surface 723, a trailing surface 725, and a peak 727 disposed between the leading surface 723 and the trailing surface 725. Similar to the peak 709, the peak 727 extends along a width of the ramp 722 and separates the leading surface 723 from the trailing surface 725. FIG. 26 is a cross-sectional view of the distal end portion 60 taken along line C-C shown in FIG. 23. The line C-C represents a plane that passes through the peak 709 of the ramp 708 and the peak 727 of the ramp 722. While peaks 709 and 727 are aligned in the example distal end portion 60 illustrated in FIG. 21-26, the scope of the disclosure is not so limited. Rather, the peaks 709 and 727 may be offset. In some instances, the peak 709 may be disposed proximally of the peak 727. In other instances, the peak 709 may be disposed distally of the peak 727.

As shown in FIG. 26, the peak 723 of the ramp 722 is disposed at an angle relative to vertical axis 729, whereas the peak 709 of the ramp 708 is parallel with the horizontal axis 731. However, in other implementations, the peak 709 may be angled relative to the horizontal axis 731. In some instances, the peak 723 may be parallel with the vertical axis 729. Referring to FIG. 22, a surface 724 corresponding to an inner surface of the passage 64 of a distal end portion 60 that omits the ramp 722 is illustrated. Consequently, the difference in topography experienced by a leading haptic, such as leading haptic 450, in instances with the ramp 722 as opposed to those without the ramp 722 is apparent. As shown in FIG. 26, the surface 710 joins with surface 724 to form a representation of a continuous surface that would otherwise exist in the passage 64 if the ramps 708 and 722 were omitted.

The freely extending end 452 of the leading haptic 450 engages the ramp 722 as the IOL 70 is advance within the passage 64 and operates to restrict distal movement of the leading haptic 450 as the leading haptic 450 is being lifted by the ramp 708. As the IOL 70 continues to advance, the leading haptic 450 engages the leading surface 723 of the ramp 722. As a result, the distal movement of the leading haptic 450 is temporarily reduced or stopped such that the leading haptic 450 is folded over the surface 726 of the optic 460. As advancement of the IOL 70 continues, a point is reached where the force applied to the leading haptic 450 in the distal direction as a result of advancement of the IOL 70 exceeds a resistive force applied to the leading haptic 450 by the ramp 722. As a result, the leading haptic 450 is deflected and forced past the ramp 722 with the leading haptic 450 folded over the optic 460 and adjacent to the surface 726. The point at which the leading haptic 450 is moved past the ramp 722 and folded over the surface 726 of the optic 460 occurs just prior to folding of the lateral sides 453 of the optic 460. The folded lateral sides 453 of the optic 460 capture the leading haptic 450 therebetween and maintain the leading optic 450 in a folded configuration.

Figure 27:
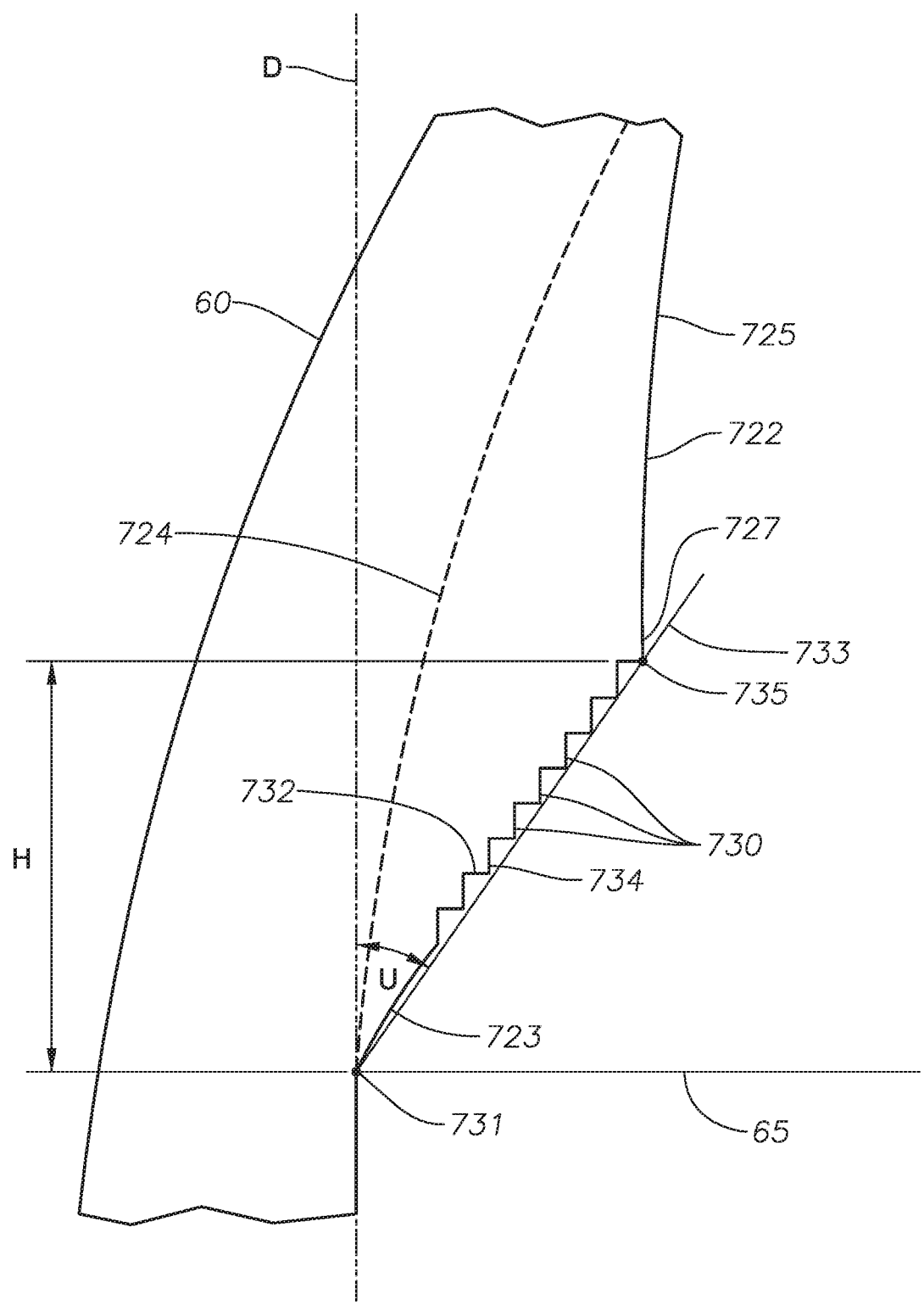
FIG. 27 is a detail view of a ramp formed in an interior passage of a distal end portion of an IOL injector.

As explained above, the ramp 708 and the ramp 722 may join into a single topographical feature present within the passage 64. In other implementations, the ramp 708 and the ramp 722 may be separate features formed in the passage 64. Further, the leading surface 723 of the ramp 722 may be a smooth surface, i.e., free discontinuities or rapid changes in curvature. However, like the leading surface 712 of the ramp 708, the leading surface 723 of the ramp 722 may have a stepped surface. FIG. 27 shows a detail view the ramp 722 shown in FIG. 22. The ramp 722 includes a stepped leading surface 723 having a plurality of steps 730. In some instances, the leading surface 723 may be formed entirely of steps 730. In other instances, the leading surface 723 may have a plurality of steps along only a portion of its length. In other implementations, the sizes of one or more steps 730 may vary from the sizes of one or more other steps 730 of the leading surface 723.

In the instances where the ramp 708 and the ramp 722 are joined, one of the leading surface 712 of the ramp 708 and the leading surface 723 of the ramp 722 may include one or more steps while the other of the leading surface 712 of the ramp 708 and the leading surface 723 of the ramp 722 may omit steps. In some instances, both the leading surface 712 and the leading surface 723 may include one or more steps. In still other implementations, both the leading surface 712 and the leading surface 723 may omit steps.

In instances wherein the leading surface 712 of the ramp 708 and the leading surface 723 of the ramp 722 include a plurality of steps, the rise and run of the steps of each of the leading surfaces 712 and 723 may be the same or the rise and run of each of the leading surfaces 712, 723 may vary from each other. Further, a slope of each of the leading surfaces 712 and 723 may be the same or different from one another. In some instances, the rise and run of the steps on each of the leading surfaces 712 and 723 may vary both between the leading surfaces 712 and 723 and on each of the leading surfaces 712 and 723.

Each of the steps 730 includes a rise 732 and a run 734. The run 734 extends in a direction parallel to a longitudinal axis 75 of the IOL injector 10, while the rise 732 extends in a direction perpendicular to the longitudinal axis 75 of the IOL injector 10. In some implementations, the rise 732 of one or more of the steps 730 may have a length in the range of 0.2 to 0.5 mm. Particularly, the length of the rise 732 may be 0.2 mm, 0.3 mm, 0.4 mm, or 0.5 mm. However, these dimensions are merely examples. In other implementations, the length of the rise 732 may be larger or smaller than the indicated range. That is, in some instances, the rise 732 may be larger than 0.5 mm or smaller than 0.2 mm. In instances where the rise 718 and run 720 of one or more of the steps 716 varies, the leading surface 712 may define an overall curved surface or, more generally, a non-linear surface.

The run 734 of one or more of the steps 730 may have a length in the range of 0.2 to 0.5 mm. Particularly, the length of the run 734 may be 0.2 mm, 0.3 mm, 0.4 mm, or 0.5 mm. However, these dimensions are merely examples. In other implementations, the length of the run 734 may be larger or smaller than the indicated range. That is, in some instances, the run 734 may be larger than 0.5 mm or smaller than 0.2 mm.

Although FIG. 27 shows an example leading surface 723 having a plurality of steps 730 that are uniform in size. Thus, in some implementations, with the leading surface 723 having a plurality of steps 730 with uniform sizes, the leading surface 723 defines a linear slope. However, the scope of the disclosure is not so limited. Rather, in other instances, one or more of the rise 732, the run 734, or both the rise 732 and run 734 of one or more of the steps 730 may be different than one or more other steps 730. In some instance, the run 734 of the steps may decrease in the distal direction along the leading surface 723. In other implementations, the run 734 of the steps may increase in the distal direction along the leading surface 723. In some instances, the rise 732 of the steps may increase in the distal direction along the leading surface 712. In other implementations, the rise 732 of the steps 730 may decrease in the distal direction along the leading surface 723. In instances where the rise 732 and run 734 of one or more of the steps 730 varies, the leading surface 723 may define an overall curved surface or, more generally, a non-linear surface. In some implementations, the stepped leading surface 723 may be arranged to form an overall parabolic shape to the leading surface 723. However, the shape of the leading surface 723 may be any desired shape. For example, the leading surface 723 may have an inclined undulating surface, an inclined flat surface, or any other desired surface.

FIG. 27 also shows a plane D that extends parallel to the longitudinal axis 75 of the IOL injector 10. The plane D passes through a first point 731 defining a proximal end of the ramp 730. An overall slope of the ramp 730 is defined by a line 733 extending from the point 71 to a point 735 wherein the line 733 tangentially touches the peak 727 of the ramp 730. The slope line 733 is angularly offset from the plane D by an angle U. In some instances, the angle U may be between 63° and 73°. Particularly, in some instances, the angle U may be 63°, 64°, 65°, 66°, 67°, 68°, 69°, 70°, 71°, 72°, or 73°. However, the angle U may be selected to be any value within the indicated range or a value larger or smaller than the indicated range.

In the illustrated example shown in FIG. 27, the ramp 722 is disposed distally of the threshold 65 between the compartment 80 and the passage 64. The ramp 708 begins at a proximal end indicated by point 731. In some instances, a longitudinal distance H between the point 731 and the peak 709 (which, in some instances, may be coincident with point 735) may be within the range of 0.4 mm to 1.4 mm. Thus, in some implementations, the distance H may be 0.4 mm, 0.5 mm, 0.6 mm, 0.7 mm, 0.8 mm, 0.9 mm, 1.0 mm, 1.1 mm, 1.2 mm, 1.3 mm, or 1.4 mm. However, the distance H may be selected to be any value within the indicated range or a value larger or smaller than the indicated range.

Referring to FIGS. 22, 26, and 27, the trailing surface 725 of the ramp 722 gradually recedes into the interior surface 724 of the third sidewall 704. In the example shown in FIG. 24, the trailing surface 725 has a positive slope as the trailing surface 725 extends distally. Similar to the trailing surface 713, discussed above, in some examples, the positive slope of the trailing surface 725 is provided for manufacturability of the IOL injector 10 and, particularly, for the distal end portion 60. In the case of injection molding, for example, a positive slope of the trailing surface 725 provides a draft angle that facilitates manufacturing of the distal end portion 60. However, the trailing surface 725 need not have a positive slope. In other implementations, the trailing surface 725 may have a neutral slope, i.e., a slope of zero, or a negative slope. In still other implementations, the trailing surface 725 of the ramp 722 may be omitted.

As shown in FIG. 26, a height F of the passage 64 may be within the range of 2.4 mm to 2.6 mm. However, such dimensions are merely illustrative, and the height F of the passage may be greater than 2.6 mm or less than 2.4 mm. Further, a height E of the ramp 722 where the ramp 722 merges into the inner surface of the passage 64 (i.e., the inner surface of the passage 64 that is a continuation of the surface 724) may be within the range of 1.5 mm to 1.8 mm. However, in some implementations, the height E may be greater than 1.8 mm or less than 1.5 mm. The height D of the ramp 708 at the peak 709 may be within the range of 0.5 mm to 1.0 mm. As is apparent, the example dimensions provided are for the indicated features at the cross-section along line C-C (shown in FIG. 27). Thus, in some implementations, the height E of the ramp 722 may be within the range of 57% to 75% of the height E of the passage 64. Also, in some implementations, the height F of the ramp 708 may be within the range of 19% and 42% of the height E of the passage 64. Again, though, the indicated ranges are illustrative only, and the heights D and E of the ramps 708 and 722, respectively, relative to the height F of the passage 64 may be selected to be any desired amount.

FIG. 28 shows another example lifting feature 800 disposed within the delivery passage 127 operable to lift the leading haptic 450 of IOL 70 over surface 726 of the optic 460. In some implementations, the lifting feature 800 may be disposed in the passage 64 of the distal end portion 60. For example, the lifting feature 800 may be attached to an upper surface (within the context of FIG. 29). That is, in some instances, the lifting feature 800 may be attached to a surface of the passage 64 that is adjacent to the interior surface 530 of the door 90 (shown in FIG. 12) and opposite the receiving surface 190 (shown in FIG. 6). In the illustrated example, the lifting feature 800 is secured to an interior surface 802 of the passage 64. The lifting feature 800 includes a base 804, a pivoting portion 806, and a hinge 808 connecting the pivoting portion 806 to the base 804. Positions I through V shown in FIG. 28 illustrate folding of the leading haptic 450 as the IOL 70 is advanced through the passage 64 relative to the optic 460.

At position I, the pivoting portion 806 of the lifting feature 800 is shown in an initial, undisturbed configuration with the leading haptic 450 just beginning to engage the pivoting portion 806. At position II, the leading haptic 450 is shown lifted in the direction of arrow 810 by an inclined surface 812 formed on the pivoting portion 806. Additionally, the lifting feature 800 also causes displacement of the leading haptic 450 towards the optic 460. In the context of advancement of the IOL 70, movement of the leading haptic 450 towards the optic 460 means that the lifting feature 800 retards or slows advancement of the leading haptic 450 relative to the optic 460, resulting in the relative movement of the leading haptic 450 towards the optic 460.

As a result of the engagement with the leading haptic 450, the pivoting portion 806 is shown slightly deflected distally in a direction of arrow 814. At position III, the leading haptic 450 is shown lifted to a maximum amount by the lifting feature 800 along with the pivoting portion 806 displaced to a greater extent distally. Position III also shows a leading edge 816 of the optic 460 positioned below the leading haptic 450 (in the context of the view shown in FIG. 28). At position IV, the leading haptic 450 is shown folded over the surface 726 and the pivoting portion 806 is further folded distally. At position V, the leading haptic 450 is shown fully folded over the surface 726 of the optic 460. The pivoting portion 806 is shown proximal of the leading haptic 450. Consequently, as the IOL 70 is advanced, a point is reached where the pivoting portion 806 pivots about hinge 808 to permit the leading haptic 450 to distally pass the folding feature 800. Thus, the folding feature 800 is operable to lift and fold the leading haptic 450 while also being operable to bend and permit the leading haptic 450 to distally move past the folding feature. As folding of the IOL 70 continues, the pivoting portion 806 remains bent about the hinge 808 to permit passage of the remainder of the IOL 70.

In some implementations, the inclined surface 812 may be a smooth surface. In other implementations, the inclined surface 812 may include a plurality of steps similar to the steps 716 shown in FIGS. 25 and 27, for example.

In some implementations, the folding feature 800 may be formed of a flexible material having a hardness less than a material forming the IOL 70. Thus, the folding feature 800 is formed of a material that permits the IOL 70 to contact and slide against the folding feature 800 but prevent damage to the folding feature. However, in other implementations, the folding feature 800 may be formed of a material having a hardness that is greater that a material forming the IOL 70. For example, the folding feature 800 may be designed so as to eliminate sharp edges to avoid damaging the IOL 70 even though the material forming the folding feature 800 has a higher hardness than the material forming the IOL 70.

Figure 29:
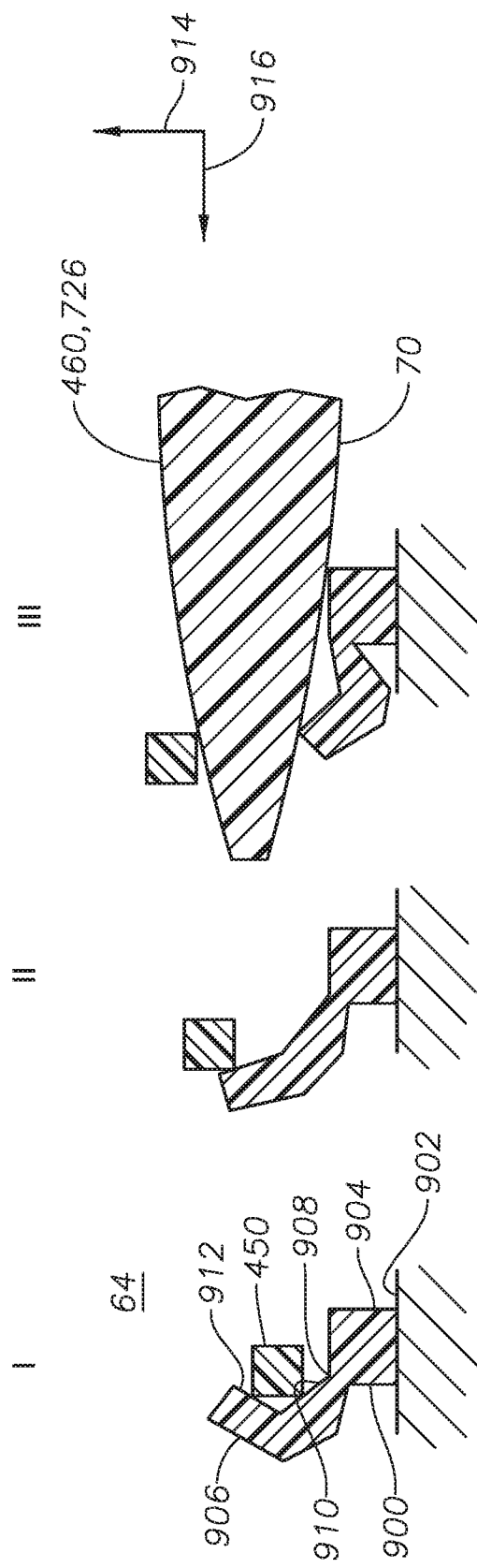
FIG. 29 shows another example lifting feature disposed within an interior passage of an IOL injector operable to lift a leading haptic of an IOL during advancement of the IOL.
Figure 30:
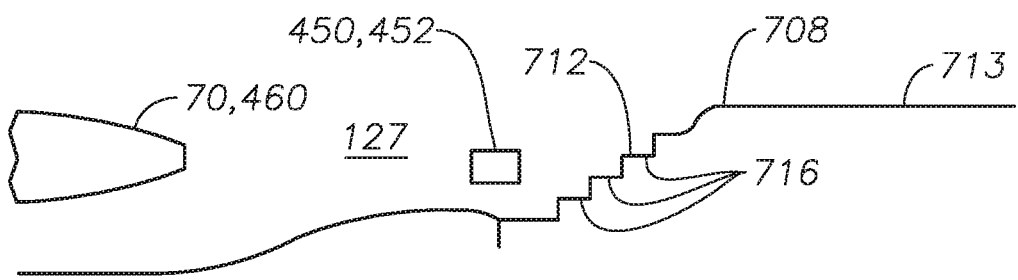
FIGS. 30-33 illustrate lifting of a leading haptic of an IOL by a ramp form on an interior surface of a distal end portion of an IOL injector as the IOL is advanced through an interior passage of the IOL injector.
Figure 31:
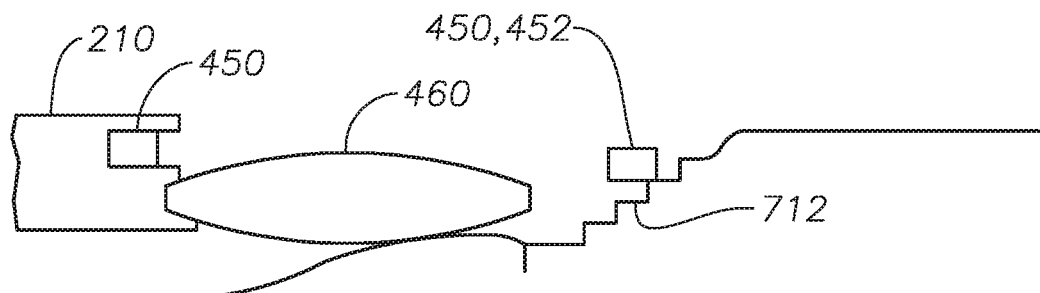
Figure 32:
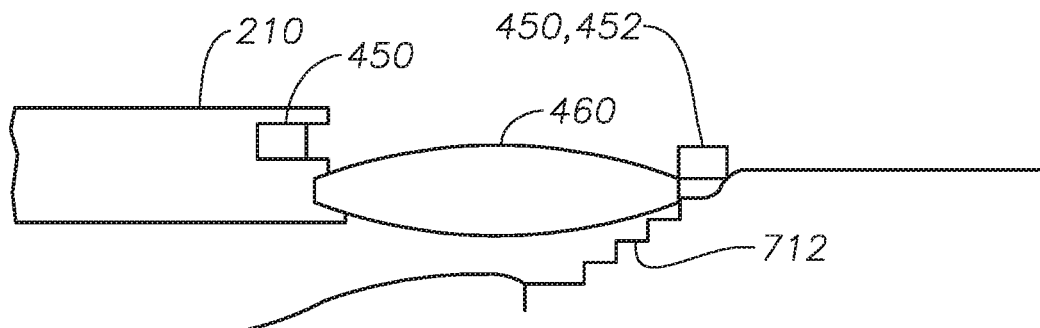
Figure 33:
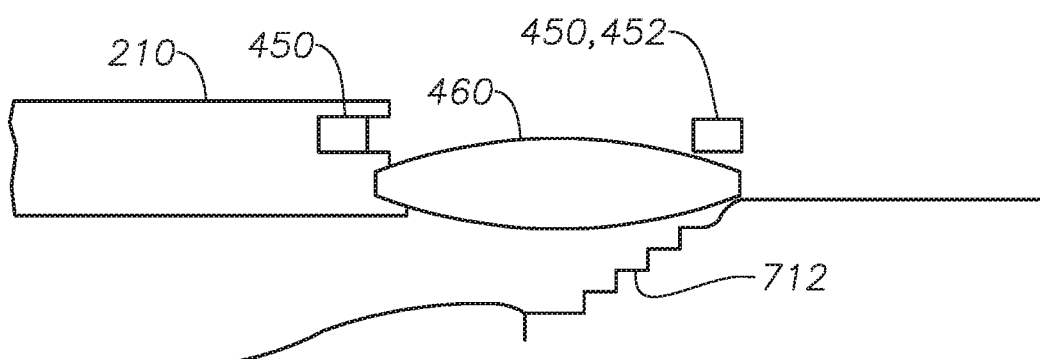

FIG. 29 illustrates another example lifting feature 900 disposed within the delivery passage 127 operable to lift the leading haptic 450 of IOL 70 over surface 726 of the optic 460. In some implementations, the lifting feature 900 may be disposed in the passage 64 of the distal end portion 60. For example, the lifting feature 900 may be attached to a lower surface (within the context of FIG. 29). That is, in some instances, the lifting feature 900 may be attached to a surface of the passage 64 that is opposite to the interior surface 530 of the door 90 (shown in FIG. 12) and adjacent the receiving surface 190 (shown in FIG. 6). In the illustrated example, the lifting feature 900 is secured to an interior surface 902 of the passage 64.

The lifting feature 900 includes a base 904, a pivoting portion 906, and a hinge 908 connecting the pivoting portion 906 to the base 904. The pivoting portion 906 has a "V" shape that defines a first inclined surface 910 and a second inclined surface 912. The leading haptic 450 of the IOL 70 engages and slides along the first and second inclined surfaces 910 and 912 so as to lift the leading haptic 450 above (in the context of FIG. 32) the surface 762 of the optic 460.

Positions I through III shown in FIG. 29 illustrate folding of the leading haptic 450 as the IOL 70 is advanced through the passage 64 relative to the optic 460. At position I, the pivoting portion 906 of the lifting feature 900 is shown in an initial, undisturbed configuration with the leading haptic 450 just beginning to engage the pivoting portion 906. At position II, the leading haptic 450 is partially folded and lifted in the direction of arrow 914 by the first and second inclined surfaces 910 and 912 formed on the pivoting portion 906. As a result of the engagement with the leading haptic 450, the pivoting portion 906 is shown deflected distally in a direction of arrow 916 relative to the base 904, resulting in the inclined surface 912 forming a ramp that operates to further lift the leading haptic 450 above the top corner of the leading edge of the optic 760 (as viewed in the context of FIG. 29). As is also illustrated at II, the lifting feature 900 also causes displacement of the leading haptic 450 towards the optic 460. In the context of advancement of the IOL 70, movement of the leading haptic 450 towards the optic 460 means that the lifting feature 900 retards or slows advancement of the leading haptic 450 relative to the optic 460, resulting in the relative movement of the leading haptic 450 towards the optic 460. At position III, the leading haptic 450 is shown lifted above and folded over the optic such that the leading haptic 450 is located adjacent to the surface 762 of the optic 460. The folding feature 900 is shown on a side of the optic 460 opposite the leading haptic 450.

In some implementations, one or both of the inclined surfaces 910 and 912 may be a smooth surface. In other implementations, one or both of the inclined surfaces 910 and 912 may include a plurality of steps similar to the steps 716 shown in FIGS. 25 and 27, for example.

As the IOL 70 continues to advance along the passage 64, the optic 460 presses against and slides over the folding feature 900 such that the pivoting portion 906 is further folded over. Similar to the folding feature 800, the folding feature 900 may be formed of a flexible material having a hardness less than a material forming the IOL 70. However, in other implementations, the folding feature 900 may be formed of a material having a hardness that is greater that a material forming the IOL 70. Similar to the folding feature 800, discussed above, in some instances, the folding feature 800 may be designed so as to eliminate sharp edges to avoid damaging the IOL 70 even though the material forming the folding feature 800 has a higher hardness than the material forming the IOL 70. Thus, the folding feature 900 is formed of a material that permits the IOL 70 to contact and slide against the folding feature 900 but prevent damage to the folding feature.

Advancement of the plunger 30 through the injector body 20 is discussed below with reference to FIGS. 1, 6, and 11. In some instances, dimensional tolerances between the plunger 30 and the injector body 20 may permit relative movement between the plunger 30 and the injector body 20 such that the distal end portion 211 is able to move within bore 40 in the direction of arrows 471, 472 (referred to hereinafter as "tolerance movement"). In instances, particularly those in which the plunger 30 includes angled portion 212, the plunger tip 220 normally remains in contact with the interior wall 298 even if the plunger 30 experiences tolerance movement as the plunger 30 advances through bore 40. Thus, in some instances, notwithstanding any tolerance movement, the plunger tip 220 remains in contact with the interior wall 298. Accordingly, the second tapered wall 303 directed and centers the plunger tip 220 into the opening 170.

If the plunger 30 experiences tolerance movement such that the plunger tip 220 no longer contacts the interior wall 298 of the bore 40, the first tapered wall 301, which includes the flexible wall portion 162, directs and centers the plunger tip 220 into the opening 170 formed at the interface 172, resulting in contact between the plunger tip 220 and the second tapered wall 303. When the plunger 30 becomes fully engaged with the injector body 20, the tolerance movement is substantially reduced or eliminated, ensuring that the plunger tip 220 remains engaged with the second tapered wall 303 and contoured ramp 180. In some instances, full engagement between the plunger 30 and the injector body 20 occurs when the cantilevered members 292 are fully engaged with the interior wall 298 of the bore 40. Consequently, in instances where tolerance movement may exist, upon full engagement between the plunger 30 and the injector body 20, the flexible wall portion 162 no longer influences the position of the plunger 30. In any case, once the plunger tip 220 advances through opening 170, the flexible wall portion 162 no longer affects the directional path of plunger 30 nor any part thereof.

As the plunger tip 220 is advanced through the compartment 80 in sliding contact with the receiving surface 190, the first groove 500 of the plunger tip 220 is positioned to engage the trailing haptic of IOL, such as trailing haptic 450 of IOL 70, as shown in FIG. 6. As the plunger tip 220 is further advanced, the plunger tip 220 encounters the contoured ramp 180 and is forced vertically towards the door 90. This vertical displacement of the plunger tip 220, while remaining in contact with the receiving surface 190, both folds the trailing haptic up over the optic of the IOL as well as align the second groove 510 of the plunger tip 220 with a trailing edge of the haptic. Particularly, the surface 502 of the plunger tip 220 contacts and displaces the haptic 450 as the plunger tip 220 is passed along the contoured surface 180, thereby folding the trailing haptic 450. As the trailing haptic 450 folds, the contoured surface 192 and wall 194 work in concert to both locate the freely extending end 452 of the trailing haptic 450 above and over the optic 460. The profile of the contoured surface 192 operates to lift the trailing haptic 450 as the plunger tip 220 is displaced towards the distal end portion 60 of the injector body 20. The wall 194 constrains lateral movement of the freely extending end 452 of the trailing haptic 450, which cause the haptic to move distally relative to the optic 460. Consequently, the trailing haptic 450 is both raised above and folded over the optic 460 as the plunger tip 220 contacts the trailing haptic 450 and follows along the contoured ramp 180. As the plunger tip 220 is further advanced, the second groove 510 accepts the trailing edge of the optic 460, and the plunger tip 220 is displaced vertically away from the door 90 due to a combination of influences from both the decreasing slope of the contoured ramp 180 and the angled portion 212 of the plunger rod 210. Movement of the plunger tip 220 in the manner described provides for improved engagement and folding of the IOL 70.

FIG. 13 is a detail view of a portion of the distal end portion 60 of the injector body 20. The distal end portion 60 includes a tapered portion 62 and the insertion depth guard 140. The distal end 265 of the biasing element 260 may engage the proximal end 50 of the injector body 20 to define a pause location of the folded or partially folded IOL. The nozzle 120 may include a demarcation 1900 that provides a visual indication of the pause position. For example, in the example shown in FIG. 13, the demarcation 1900 is a narrow ridge or line that encircles all or a portion of the distal end portion 60. In some instances, the demarcation 1900 may be disposed between the tapered portion 62 and the insertion depth guard 140. At least a portion of the injector body 20 may be formed form a transparent or semi-transparent material that permits a user to see an IOL within the injector body 20. Particularly, the distal end portion 60 of the injector body 20 may be formed from a transparent material to permit observation of the IOL as it is moved therethrough by the plunger 30.

FIG. 14 shows a view of the distal end portion 60 of the IOL injector 10 with IOL 70 located therein at a pause position. As shown in FIG. 14, the pause position of the IOL may be defined as a location where the distal edge 462 of optic 460 of the IOL 70 substantially aligns with the demarcation 1900. A haptic 450 or a portion thereof may extend beyond the demarcation 1900. Again, the pause position may also correspond to the initial engagement of the distal end 265 of the biasing element 260 with the proximal end 50 of the injector body 20. Therefore, the pause location may be jointly indicated by positioning of the IOL, or part thereof, relative to the demarcation 1900 and the initial contact between the distal end 265 of the biasing element 260.

In other instances, a location of the IOL relative to the distal opening 12 of the nozzle 120 when the distal end 265 of the biasing element 260 contacts the proximal end 50 of the injector body 20 may vary. In some instances, the IOL may be partially ejected from the distal opening 125 when the distal end 265 of the biasing element 260 contacts the proximal end 50 of the injector body 20. For example, in some instances, approximately half of the IOL may be ejected from the distal opening 125 when the distal end 265 of the biasing element 260 contacts the proximal end 50 of the injector body 20. In other instances, the IOL may be contained wholly within the IOL injector when the distal end 265 of the biasing element 260 contacts the proximal end 50 of the injector body 20.

FIG. 15 shows a cross sectional view of the opening 170 formed at the interface 172. In some instances, the opening 170 may define a "T" shape. The plunger tip 220 is shown disposed at the opening 170 with the flexible wall portion 162 contacting a surface 214 the plunger rod 210. In some instances, the cross section of the plunger rod 210 increases towards the proximal end of the plunger rod 210. Thus, as the plunger rod 210 is advanced through the opening 170, the plunger rod 210 fills the opening as a result of the increasing cross section. Portions 173 and 175 of the opening 170 are filled by flanges 213, 215 (shown in FIG. 9).

Figure 16:
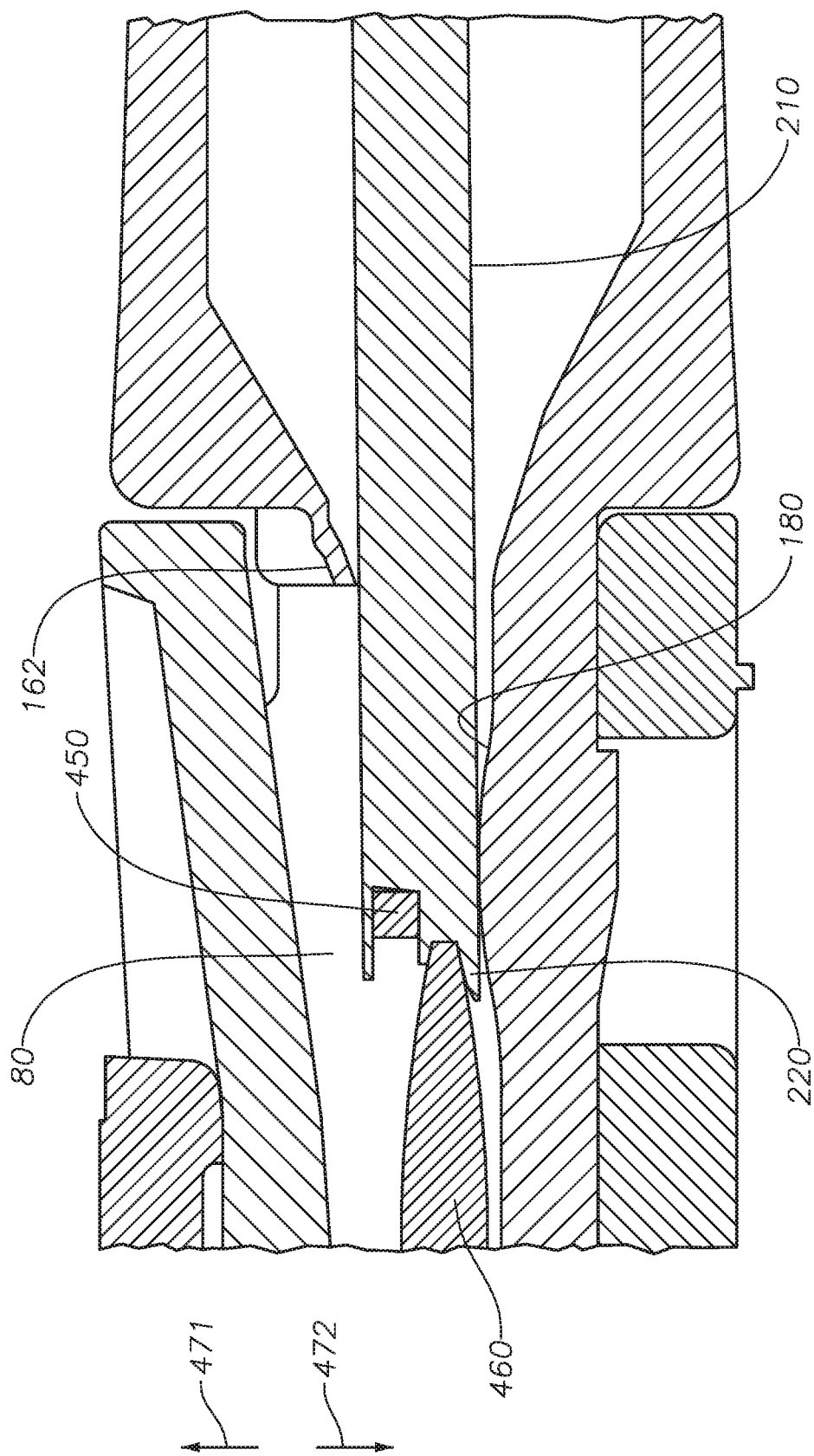
FIG. 16 is a partial cross-sectional view of an example IOL injector.

As the opening 170 is filled by the increasing cross section of the plunger rod 210 as the plunger rod 210 is advanced distally through the injector body 20, the flexible wall portion 162 is flexed in the direction of arrow 471 to permit passage of the plunger rod 210, as shown in FIG. 16. Further, as a result of the angled portion 212 of the plunger rod 210, the contoured ramp 180, and the folding of IOL 70 as it is advanced through the IOL injector 10, the plunger tip 220 is made to follow a defined path through the compartment 80, the distal end portion 60, and nozzle 120 uninfluenced by the flexible wall portion 162.

FIG. 16 shows the flexible wall portion 162 being flexed in the direction of 471 as the plunger rod 210 continues to advance distally through the IOL injector 10. Further, FIG. 16 also shows the plunger tip 220 engaged with IOL 70 such that trailing haptic 450 is received into the first groove 500 at a location offset from the second groove 510, and the proximal edge of the optic 460 is received into the second groove 510.

As the IOL 70 is advanced through the passage 64 of the distal end portion 60, the IOL 70 is folded into a reduced size to permit passage of the IOL 70 through the nozzle 120 and into the eye. During folding of the IOL 70, a resistive force on the plunger 30 is increased. Once the IOL 70 is fully folded 70, the resistive force on the plunger 30 generally reduces.

A wound may be formed in the eye. The wound may be sized to accommodate the nozzle 120 of the IOL injector 10. The nozzle 120 may be inserted into the wound. The nozzle 120 may be advanced through the wound until the flanged surface 150 of the insertion depth guard 140 abuts the exterior surface of the eye. Contact between the insertion depth guard 140 and the exterior surface of the eye limits the depth to which the nozzle 120 may be inserted into the eye, preventing unnecessary stress on the edges of the wound as well as preventing enlargement of the wound due to over insertion of the IOL injector 10. Consequently, the insertion depth guard 140 operates to reduce additional trauma to the eye and enlargement of the wound.

With the nozzle properly positioned within the eye through the wound, the user may complete delivery of the folded IOL into the eye. Referring to FIG. 2, as advancement of the plunger 30 continues, the biasing element 260 is compressed. Compression of biasing element 260 increases a resistive force to advancement of the plunger 30, also referred to as plunging force. This additional resistance to advancement of the plunger 30 diminishes changes to the plunging force associated with the folding of the IOL prior to insertion into the eye. Further, in some instances, the biasing element 260 may be made to contact the injector body 120 when, or proximate to when, the IOL 70 has fully folded so that the a reduction in resistive force that may result from the IOL 70 being fully folded may be offset by the compression of the biasing element 260. This increase in resistive force provided by compression of the biasing element 260, particularly in light of a reduction that may result due to the IOL 70 being fully folded, provides improved tactile feedback to a user, such as a medical profession, during delivery of the IOL 70 into an eye. This improved tactical feedback provides the user with improved control during delivery of the IOL 70, which may prevent rapid expulsion of the IOL 70 into the eye.

As a result, the user is able to provide a smooth application of force without experiencing any sudden or rapid changes in advancement of the plunger 30. Such sudden or rapid changes may result in the IOL being rapidly expelled from an injector. Rapid expulsion of an IOL into an eye may cause damage, such as perforation of the capsular bag. Such damage may increase the time required to compete the surgical procedure and may increase the harm caused immediately and post operatively to the patient. Upon insertion of the IOL into the eye, the IOL injector 10 may be withdrawn from the eye.

Although the disclosure provides numerous examples, the scope of the present disclosure is not so limited. Rather, a wide range of modification, change, and substitution is contemplated in the foregoing disclosure. It is understood that such variations may be made to the foregoing without departing from the scope of the present disclosure.

What is claimed is:

1. An intraocular lens (IOL) injector comprising:
   an injector body comprising:
      a bore defined by an interior wall;
      a longitudinal axis extending centrally along the injector body;
      a distal end portion comprising:
         a first sidewall;
         a second sidewall disposed opposite the first sidewall;
         a third sidewall extending between the first sidewall and the second sidewall; and
         a fourth sidewall opposite the third sidewall, the first sidewall, second sidewall, third sidewall, and fourth sidewall joined to define a passage forming a portion of the bore;
      a first ramp formed on an interior surface of the passage along the first sidewall and laterally offset from the longitudinal axis, the first ramp disposed at a position within the passage to contact a leading haptic of an intraocular lens, the first ramp comprising:
         a first distal leading surface being sloped and inwardly extending from the interior surface into the passage; and
         a first peak disposed at a distal end of the first ramp disposed at a distal end of the distal first leading surface;
   a plunger slideable in the bore;
   a compartment configured to receive the IOL, wherein the IOL comprises a center optic portion and a first haptic arm and a second haptic arm on substantially opposing sides of the center optic, wherein the compartment adjoins the passage, and wherein the compartment is configured to house the IOL such that the first haptic arm is in a distal leading position with respect to the longitudinal axis followed by the center optic and the second haptic arm in a trailing position,
   wherein the passage is varied in size such that the center optic of the IOL is folded when advanced through the passage by the plunger, and wherein the ramp is configured such that the first haptic arm in the distal leading position is sufficiently raised over the center optic by the ramp prior to the center beginning to fold due to the varied size of the passage.

2. The intraocular lens injector of claim 1, wherein the first leading surface comprises a first plurality of steps therealong.

3. The intraocular lens injector of claim 2, wherein each of the first plurality of steps comprises a rise and a run.

4. The intraocular lens injector of claim 3, wherein the rise and run of each of the steps is uniform.

5. The intraocular lens injector of claim 3, wherein at least one of the rise and run of at least one step of the first plurality of steps is different from the rise and the run of another of the steps of the first plurality of steps.

6. The intraocular lens injector of claim 1 further comprising a second ramp formed on the interior surface of the passage along the second sidewall and adjacent to the first ramp.

7. The intraocular lens injector of claim 6, wherein the first ramp and the second ramp are integrally formed.

8. The intraocular lens injector of claim 6, wherein the second ramp comprises a second leading surface, wherein the second leading surface is sloped and extends inwardly from the interior surface of the passage.

9. The intraocular lens injector of claim 8, wherein the second ramp further comprises a second peak disposed at a distal end of the second leading surface.

10. The intraocular lens injector of claim 8, wherein the second leading surface comprises a second plurality of steps.

11. The intraocular lens injector of claim 10, wherein each of the second plurality of steps comprises a rise and a run.

12. The intraocular lens injector of claim 11, wherein the rise and run of each of the steps is uniform.

13. The intraocular lens injector of claim 11, wherein at least one of the rise and run of at least one step of the second plurality of steps is different from the rise and the run of another of the steps of the second plurality of steps.

14. The intraocular lens injector of claim 8, wherein the first leading surface and the second leading surface are integrally formed.

15. The intraocular lens injector of claim 1, wherein the first ramp further comprises a first trailing surface disposed distally of the first peak.

16. The intraocular lens injector of claim 15, wherein further comprising a second ramp formed on the interior surface of the passage along the second sidewall and adjacent to the first ramp, wherein the second ramp comprises:
   a second leading surface that is sloped and that extends inwardly from the interior surface of the passage;
   a second peak disposed at a distal end of the second leading surface; and
   a second trailing surface,
   wherein the second trailing surface has a positive slope.

17. The intraocular lens injector of claim 16, wherein the first trailing surface and the second trailing surface are integrally formed.

18. The intraocular lens injector of claim 1, wherein the first trailing surface has a positive slope.

\* \* \* \* \*